US008193382B2

(12) United States Patent
Lilga et al.

(10) Patent No.: US 8,193,382 B2
(45) Date of Patent: Jun. 5, 2012

(54) HYDROXYMETHYL FURFURAL OXIDATION METHODS

(75) Inventors: Michael A. Lilga, Richland, WA (US);
Richard T. Hallen, Richland, WA (US);
Jianli Hu, Overland Park, KS (US);
James F. White, Richland, WA (US);
Michel J. Gray, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 79 days.

(21) Appl. No.: 12/712,100

(22) Filed: Feb. 24, 2010

(65) Prior Publication Data

US 2010/0152470 A1 Jun. 17, 2010

Related U.S. Application Data

(62) Division of application No. 11/932,436, filed on Oct. 31, 2007, now Pat. No. 7,700,788.

(60) Provisional application No. 60/863,704, filed on Oct. 31, 2006.

(51) Int. Cl.
*C07D 307/48* (2006.01)

(52) U.S. Cl. ...................................... 549/489

(58) Field of Classification Search .................. 549/483, 549/484, 488, 489
See application file for complete search history.

(56) References Cited

U.S. PATENT DOCUMENTS

| | | |
|---|---|---|
| 3,326,944 A | 6/1967 | Lew |
| 4,549,025 A | 10/1985 | Dalcanale et al. |
| 4,897,497 A | 1/1990 | Fitzpatrick |
| 4,977,283 A | 12/1990 | Leupold et al. |
| 5,608,105 A | 3/1997 | Fitzpatrick |
| 5,892,107 A | 4/1999 | Farone et al. |
| 6,706,900 B2 | 3/2004 | Grushin et al. |
| 6,790,997 B2 | 9/2004 | Eckert et al. |
| 7,956,203 B2 | 6/2011 | Grushin et al. |
| 2003/0055271 A1 | 3/2003 | Grushin et al. |

FOREIGN PATENT DOCUMENTS

| | | |
|---|---|---|
| DE | 3826073 A1 | 7/1988 |
| EP | 0356703 A | 3/1990 |
| FR | 2669636 A1 | 5/1992 |
| GB | 2188927 A | 10/1987 |
| JP | 55049368 A | 4/1980 |

(Continued)

OTHER PUBLICATIONS

Durst, Experimental Organic Chemistry, table 4.1, 1980, McGraw-Hill, Inc., p. 146-147, in 4 total pages including a cover sheet.*

(Continued)

*Primary Examiner* — Taylor Victor Oh
(74) *Attorney, Agent, or Firm* — Wells St. John P.S.

(57) ABSTRACT

A method of oxidizing hydroxymethylfurfural (HMF) includes providing a starting material which includes HMF in a solvent comprising water into a reactor. At least one of air and $O_2$ is provided into the reactor. The starting material is contacted with the catalyst comprising Pt on a support material where the contacting is conducted at a reactor temperature of from about 50° C. to about 200° C. A method of producing an oxidation catalyst where $ZrO_2$ is provided and is calcined. The $ZrO_2$ is mixed with platinum (II) acetylacetonate to form a mixture. The mixture is subjected to rotary evaporation to form a product. The product is calcined and reduced under hydrogen to form an activated product. The activated product is passivated under a flow of 2% $O_2$.

10 Claims, 39 Drawing Sheets

FOREIGN PATENT DOCUMENTS

| | | |
|---|---|---|
| JP | 02068569 A | 3/1990 |
| JP | 03101672 A | 4/1991 |
| SU | 282331 A | 9/1970 |
| WO | 03024947 A1 | 3/2003 |

OTHER PUBLICATIONS

Verdeguer et al, Catalytic Oxidation of HMF into Furan -2,5-dicarboxylic acid , Journal of Catalysis, 1993, p. 327-344, translated.*

Carlini et al., "Selective oxidation of 5-hydroxymethyl-2-furaldehyde to furan-2,5-dicarboxaldehyde by catalytic systems based on vanadyl phosphate" Applied Catalysis A: General 289 (2005) 197-204.

Ribeiro et al., "Cooperative effect of cobalt acetylacetonate and silica in the catalytic cyclization and oxidation of fructose to 2,5-furandicarboxylic acid" Catalysis Communications 4 (2003) 83-86.

Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalyats", Adv, Synth, Catal. 2001, 343, No. 1, 102-111.

Kroger et al., "A new approach for the production of 2,5-furandicarboxylic acid by in situ oxidation of 5-hydroxymethylfurfural starting from fructose", Topics in Catalysis 13 (2000) 237-242.

Baradii et al., "Selective electrocatalytic oxidation of 2,5-dihydroxymethylfuran in aqueous medium: a chromatographic analysis of the reaction products", Electrochimica Acta 44 (1999) 2779-2787.

Moreau et al., "Selective oxidation of 5-hydroxymethylfurfural to 2,5-furandicarboxaldehyde in the presence of titania supported vanadia catalysts", Studies in Surface Science and Catalysis vol. 108, Heterogeneous Catalysis and Fine Chemicals IV, 1997, 399-406.

Van Deurzen et al., "Chloroperoxidase-Catalyzed Oxidation of 5-Hydroxymethylfurfural", J. Carbohydrate Chemistry, 16(3), 299-309 (1997).

Krupenskii,V. I., "Oxidation of hydroxymethylfurfural by copper(II) and iron(III) ions", Izvestiya Vysshikh Uchebnykh Zavedenii, Khimiya i Khimicheskaya Tekhnologiya (1981), 24(5), 553-5. ISSN:0579-2991.

Skowronski et al., "Selective Anodic Oxidation of 5-Hydroxymethylfurfural", Synthesis, Nov. 1996, 1291-1292.

Cataldi et al., "Electrocatalytic Oxidation and Amperometric Detection of Aliphatic and Furanic Aldehydes at a Mixed-Valent Ruthenium Oxide-Ruthenium Cyanide Film on Glassy Carbon Electrodes", Anal. Chem., 1995, 67, 3740-3745.

Cottier et al., "Synthesis of Furan-2,5-Dicarbaldehyde by Oxidation of 5-Silyloxymethyl-2-Furfural", Synthetic Communications, 24(7), 939-944 (1994).

Cottier et al., "Oxidation of 5-Hydroxymethylfurfural and Derivatives to Furanaldehydes with 2,2,6,6-Tetramethylpiperidine Oxide Radical—Co-oxidant Pairs", May-Jun. 1995, J. Heterocyclic Chem., 32, 927-930.

Cottier et al., "Oxidation of 5-Hydroxymethylfurfural under Sonochemical Conditions", Polish J. Chem., 68, 693-698, 1994.

Grabowski et al., "The Electrochemical Oxidation of 5-Hydroxymethylfurfural with the Nickel Oxide/Hydroxide Electrode", Electrochimica Acta, vol. 36, No. 13, p. 1995, 1991.

Verdeguer et al., "Oxydation catalytique du HMF en acide 2,5-furane dicarboxylique", Journal of Molecular Catalysis, 85 (1993) 327-344.

Krupenskii, V. I., "Oxidation of furanoid aldehydes by palladium (II)", Zhurnal Obshchei Khimii (1996), 66(11), 1874-1875, ISSN: 0044-460X.

Krupenskii, V. I., "Oxidation of hydroxymethylfurfural by transition metal ions in an acid medium", Zhurnal Obshchei Khimii (1983), 53(4), 903-6, ISSN: 0044-460X.

Morikawa, "Synthesis of hydroxymethylfurfural and 2,5-furandicarboxaldehyde", Noguchi Kenkyusho Jiho (1978), 21, 25-33, ISSN: 0369-5131.

Morikawa, "Synthesis of 2,5-furandicarboxaldehyde from 5-hydroxymethylfurfural", Noguchi Kenkyusho Jiho (1979), (22), 20-7, ISSN: 0369-5131.

Kawana et al., "Electrooxidation of 5-hydroxymethylfurfural and its derivatives", Nippon Kagaku Kaishi (1963), (12), 1747-52, ISSN: 0369-4577.

Leupold et al., "Catalytic oxidation of 5-(hydroxymethyl)furfural", Chemical Abstracts, vol. 113, 1990, p. 638.

Lewkowski, "Synthesis, Chemistry and Applications of 5-Hydroxymethyl-furfural and its Derivatives", General Papers, Arkivoc 2001 (i) 17-54, ISSN 1424-6376.

El Hajj et al., "Synthese de l'hydroxymethyl-5 furanne carboxaldehyde-2 et de ses derives par traitement acide de sucres sur resines echangeuses d'ions", Bull. Soc. Chim. Fr., 855-860, 1987.

Deeba et al: "Stabilization of platinum on silica promoted with lanthanum oxide and zirconium oxide" Applied Catalysis A: General, Elsevier Science, Amsterdam, NL, vol. 124, No. 2, Apr. 13, 1995, pp. 339-344, XP022249836 ISSN: 0926-860X.

Reyes, P. et al., "The nature of the support and the metal precursor on the resistance to sulphur poisoning of Pt supported catalysts", Applied Catalysis A: General vol. 163, No. 1-2 (Dec. 5, 1997), pp. 145-152.

Huber, Florian et al., "Remarks on the passivation of reduced Cu-, Ni-, Fe-, Co-based catalysts", Catalysis Letters vol. 110, Nos. 3-4, Sep. 1, 2006, pp. 211-220.

Reyes, P. et al., "The effect of Mo on the catalytic and surface properties of Rh-Mo/ZrO2 catalysts", Catalysis Letters vol. 34, 1995, pp. 331-341.

WO PCT/US07/023063IPRP, filed May 5, 2009, Battelle Memorial Institute.

WO PCT/US07/023063Search Report, filed Jun. 23, 2008, Battelle Memorial Institute.

WO PCT/US07/023063Written Opinion, filed Jun. 23, 2008, Battelle Memorial Institute.

* cited by examiner

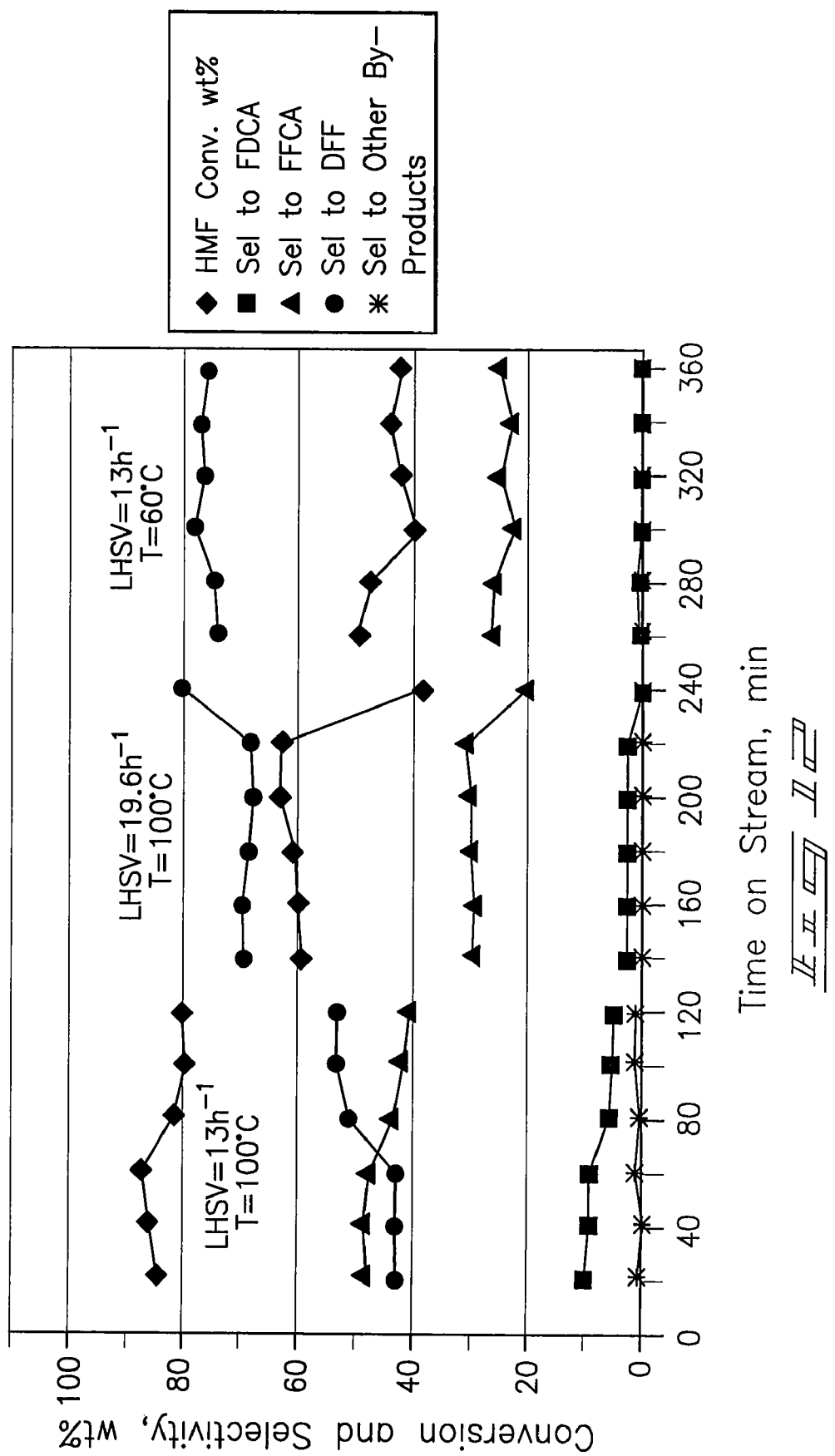

_US 8,193,382 B2_

HYDROXYMETHYL FURFURAL OXIDATION METHODS

RELATED PATENT DATA

This patent resulted from a divisional of U.S. patent application Ser. No. 11/932,436 which was filed on Oct. 31, 2007 which claims priority under 35 U.S.C. §119 to U.S. Provisional Application No. 60/863,704, which was filed Oct. 31, 2006.

TECHNICAL FIELD

The invention pertains to hydroxymethylfurfural oxidation methods, methods of producing diformyl furan and methods of producing an oxidation catalyst.

BACKGROUND OF THE INVENTION

Hydroxymethylfurfural (HMF) is a compound which can be produced from various hexoses or hexose-comprising materials. HMF can in turn be converted into a variety of derivatives, many of which are currently or are quickly becoming commercially valuable. Oxidation of HMF can produce oxidation products including diformyl furan (DFF), hydroxymethyl furan carboxylic acid (HMFCA), formylfuran carboxylic acid (FFCA), and furandicarboxylic acid (FDCA). Uses for these oxidation products include but are not limited to adhesives, sealants, composites, coatings, binders, foams, curatives, monomers and resins.

Although numerous routes and reactions have been utilized for preparing one or more of the oxidation products set forth above, conventional methodology typically results in low HMF conversion, low product selectivity and/or low product yield. It is desirable to develop alternative methodologies for oxidation of HMF and production of HMF oxidation products.

SUMMARY OF THE INVENTION

In one aspect the invention pertains to a method of oxidizing hydroxymethylfurfural (HMF). The method includes providing a starting material which includes HMF in a solvent comprising water into a reactor. At least one of air and $O_2$ is provided into the reactor. The starting material is contacted with the catalyst comprising Pt on a support material where the contacting is conducted at a reactor temperature of from about 50° C. to about 200° C.

In one aspect the invention pertains to a method of producing diformylfuran. The method includes providing a mixture comprising HMF and an organic solvent. The mixture is contacted with a catalyst comprising active γ-$MnO_2$. The mixture is subjected to reflux temperature for a time of from about 6 hours to about 12 hours.

In one aspect the invention includes a method of producing an oxidation catalyst. $ZrO_2$ is provided and is calcined. The $ZrO_2$ is mixed with platinum (II) acetylacetonate to form a mixture. The mixture is subjected to rotary evaporation to form a product. The product is calcined and reduced under hydrogen to form an activated product. The activated product is passivated under a flow of 2% $O_2$.

BRIEF DESCRIPTION OF THE DRAWINGS

Preferred embodiments of the invention are described below with reference to the following accompanying drawings.

FIG. 10 shows HMF conversion and product selectivity as a function of time on stream utilizing the catalyst of FIG. 1 at P=150 psig air, T=100° C., 1% HMF, LHSV=7.5-15 $h^{-1}$, GHSV=300 $h^{-1}$.

FIG. 12 shows conversion of HMF and selective production of the indicated products as a function of time on stream utilizing a continuous flow reactor with a 5% Pt supported on $SiO_2$ catalyst and a base set of parameters in accordance with one aspect of the invention; 1% HMF, 150 psig air, 60-100° C., LHSV=13-19.6 $h^{-1}$, GHSV=261 $h^{-1}$.

FIG. 13 shows HMF conversion and product selectivity as a function of time on stream utilizing the catalyst of FIG. 12 in the presence of 0.8% $Na_2CO_3$. (1% HMF, 0.8% $Na_2CO_3$, 150 psig air, 100° C., LHSV=13-6.5 $h^{-1}$, GHSV=261 $h^{-1}$.)

Na$_2$CO$_3$ added to 1% HMF LHSV=7.5-15 h$^{-1}$, air GHSV=300 h$^{-1}$, catalyst reduced at 30° C. wet.

Figure 1:
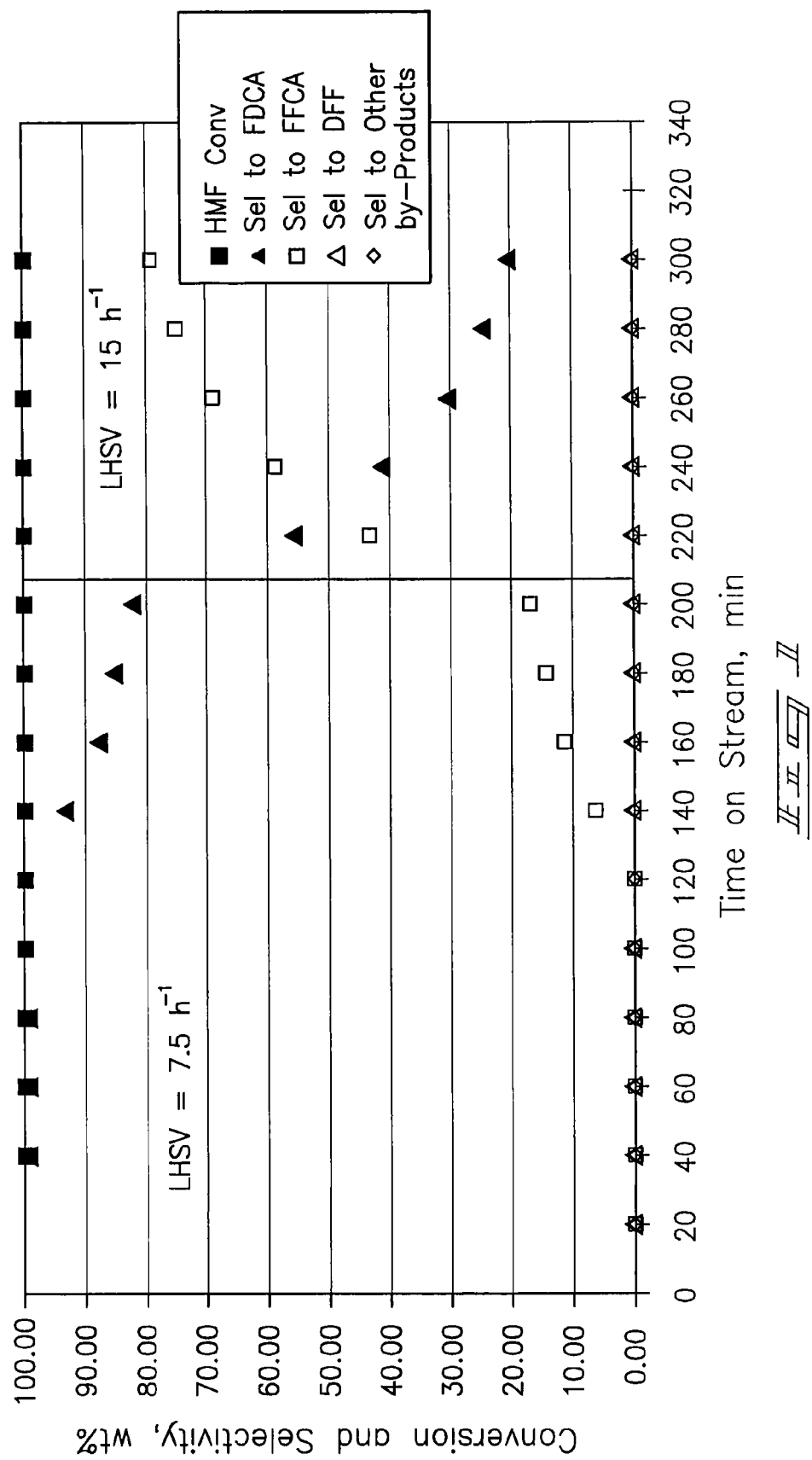
FIG. 1 shows conversion of HMF and selective production of furan dicarboxylic acid and formylfuran carboxylic acid as a function of time on stream utilizing a continuous flow reactor with a 5% platinum supported on carbon catalyst and a base set of parameters in accordance with one aspect of the invention. The parameters included P=150 psig, T=100° C., 0.828% $Na_2CO_3$ added to 1% HMF, liquid hourly space velocity (LHSV)=7.5-15 $h^{-1}$, air gas hourly space velocity (GHSV)=300 $h^{-1}$, catalyst reduced at 30° C. wet.
Figure 2:
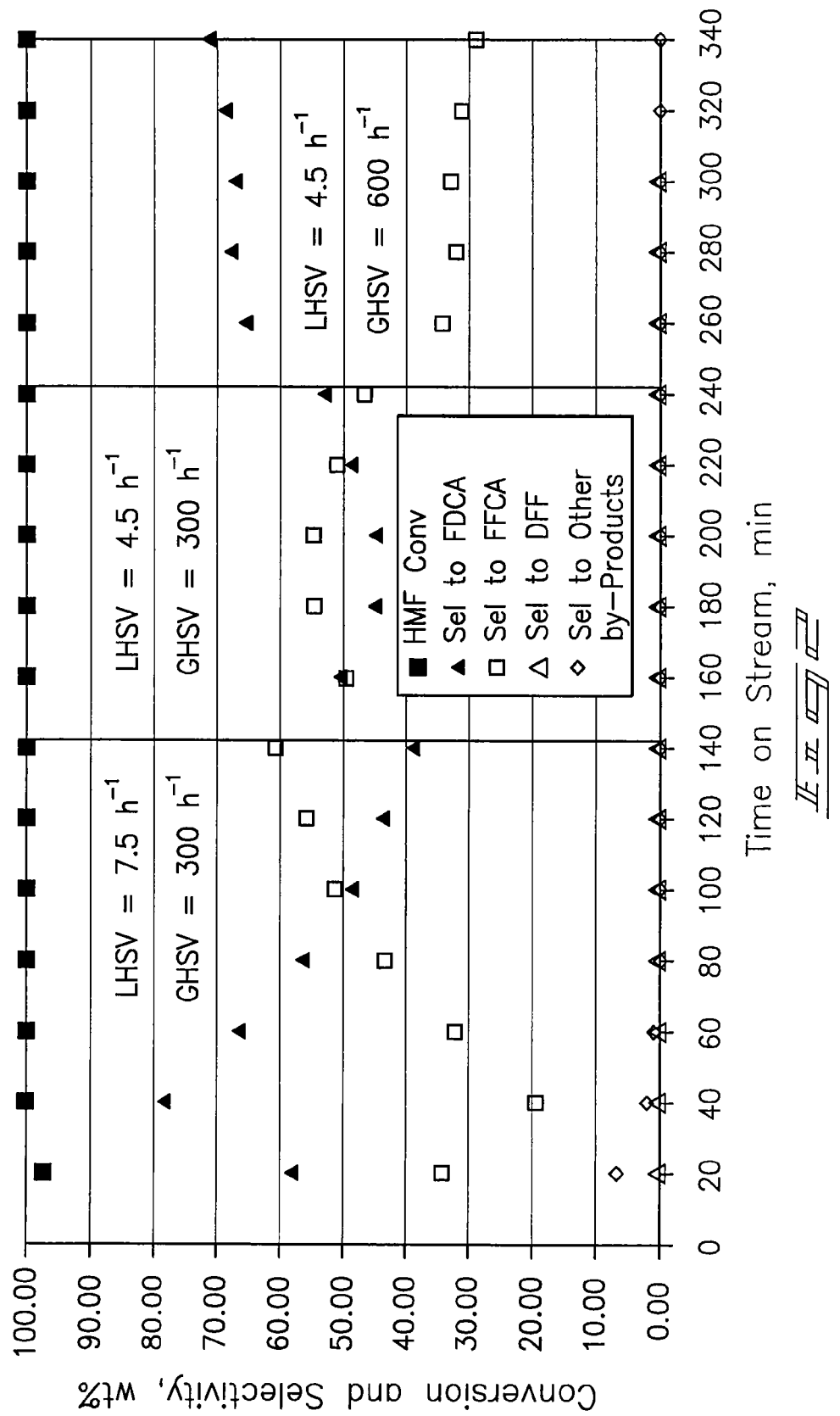
FIG. 2 shows HMF conversion and product selectivity as a function of time on stream using the catalyst of FIG. 1 at a decreased temperature (T=70° C.), LHSV=4.5-7.5 $h^{-1}$ and air GHSV=300-600 $h^{-1}$ (all other parameters and conditions being as set forth above with respect to FIG. 1).
Figure 3:
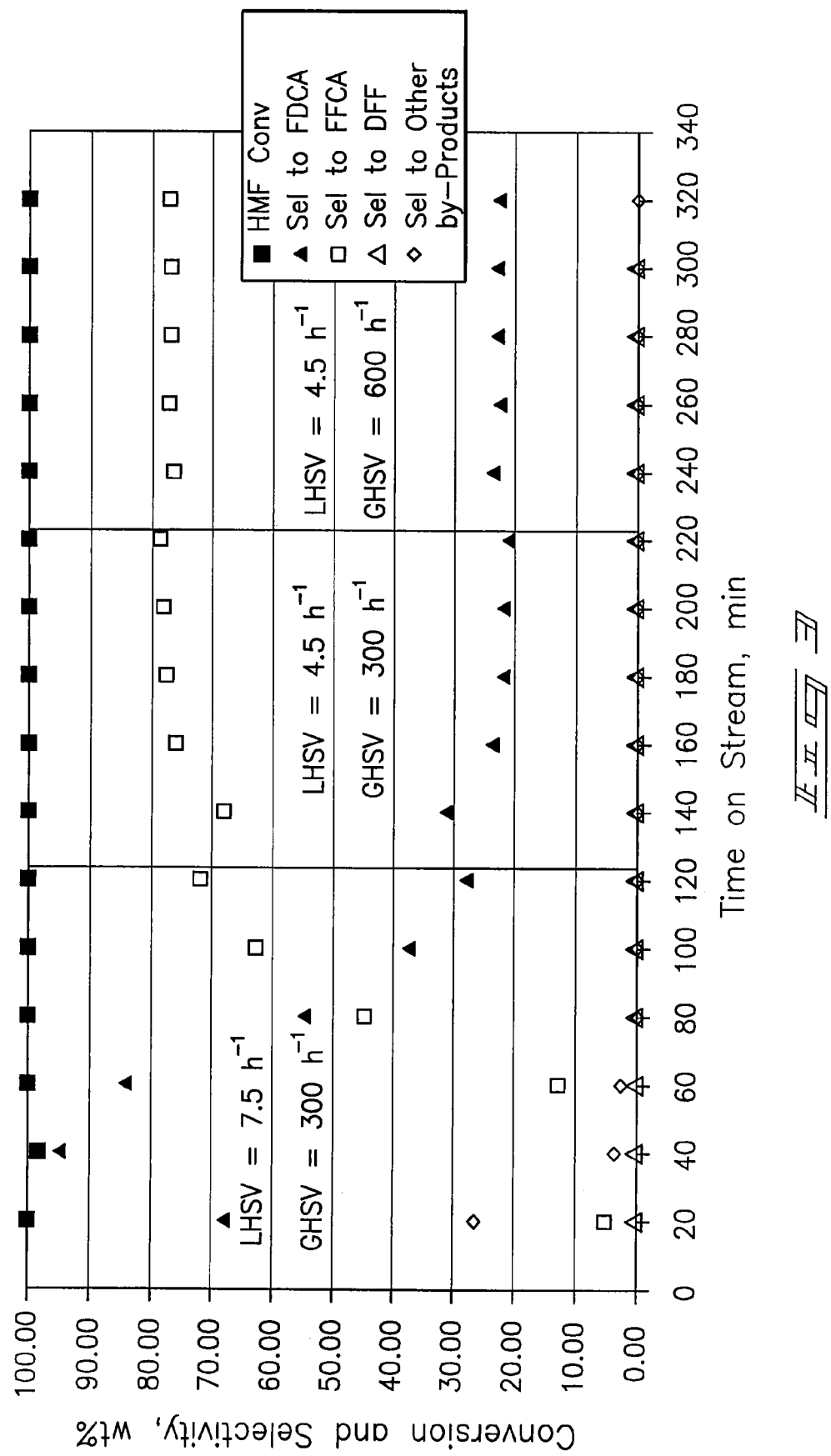
FIG. 3 shows HMF conversion and product selectivity as a function of time on stream utilizing the catalyst of FIG. 1 and the parameters as set forth for FIG. 2 except for temperature (T=50° C.).
Figure 4:
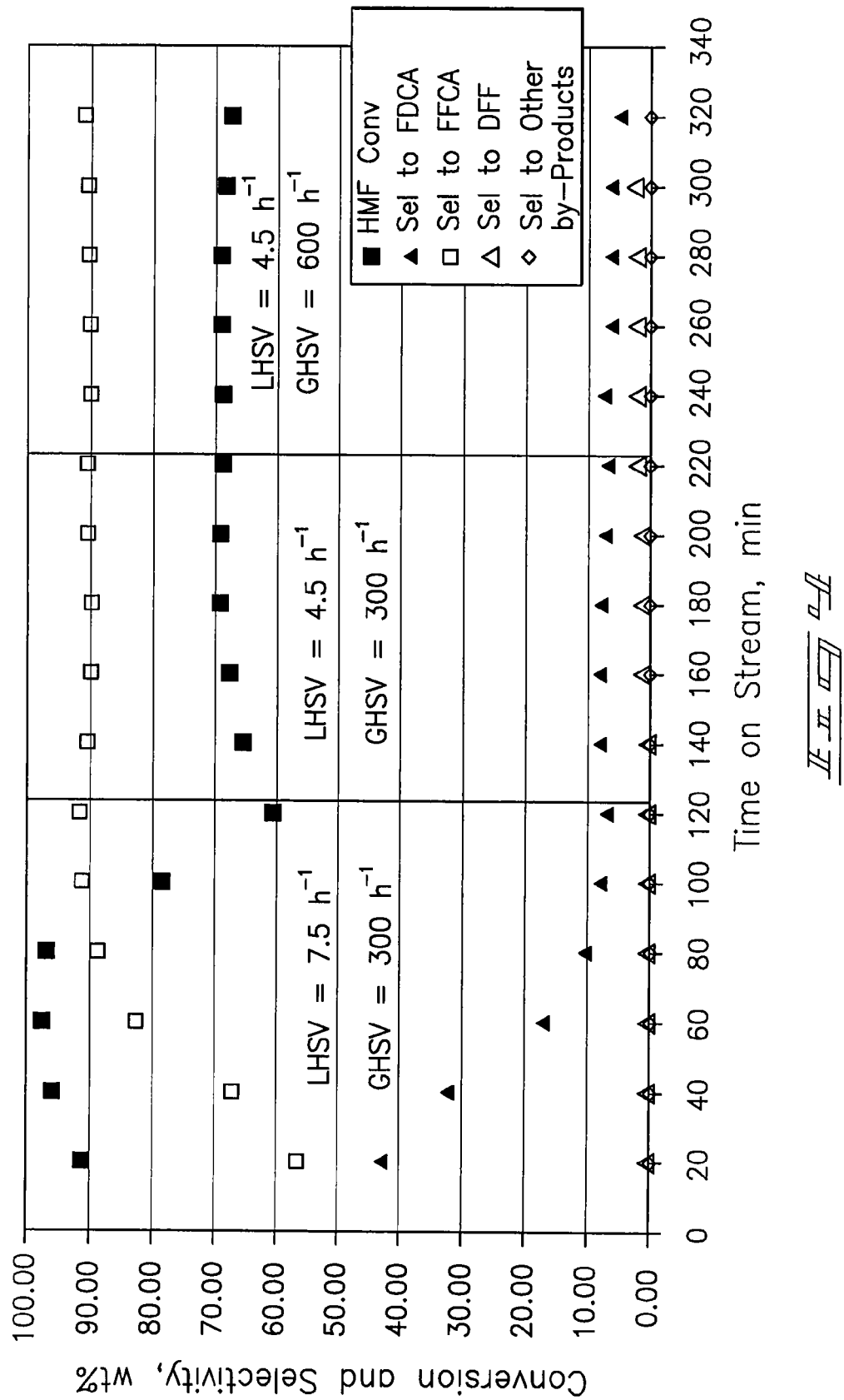
FIG. 4 shows HMF conversion and product selectivity as a function of time on stream utilizing the catalyst of FIG. 1 and the conditions as set forth at FIG. 2 with the exception of the temperature which was T=30° C.
Figure 5:
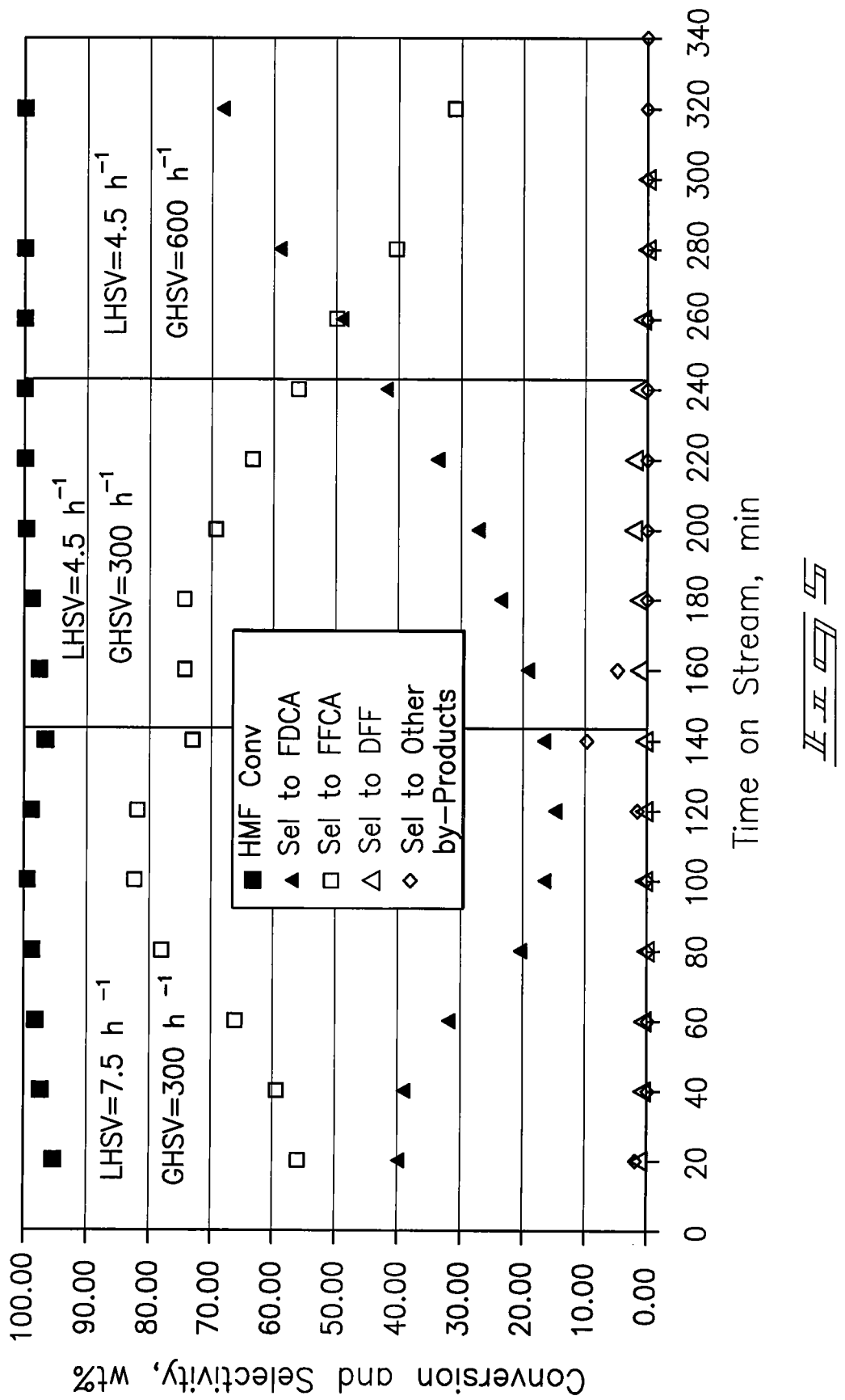
FIG. 5 shows HMF conversion and product selectivity as a function of time on stream utilizing the catalyst of FIG. 1 and the conditions of FIG. 2 with a decreased concentration of $Na_2CO_3$ of 0.414% and T=100° C.
Figure 6:
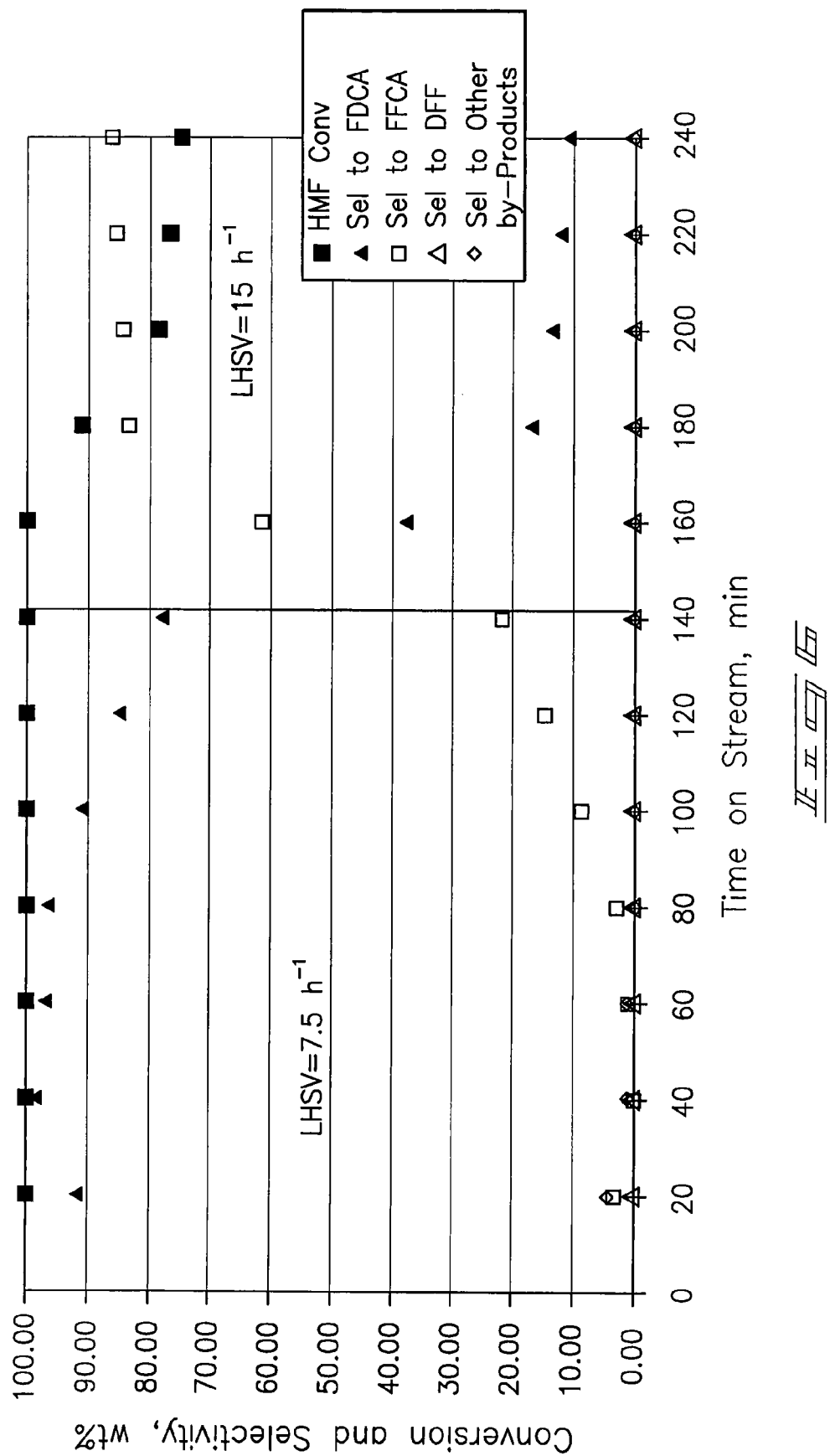
FIG. 6 shows HMF conversion and product selectivity as a function of time on stream utilizing the catalyst of FIG. 1 and the conditions of FIG. 1 except with an increased $Na_2CO_3$ concentration of 1.66%.
Figure 7:
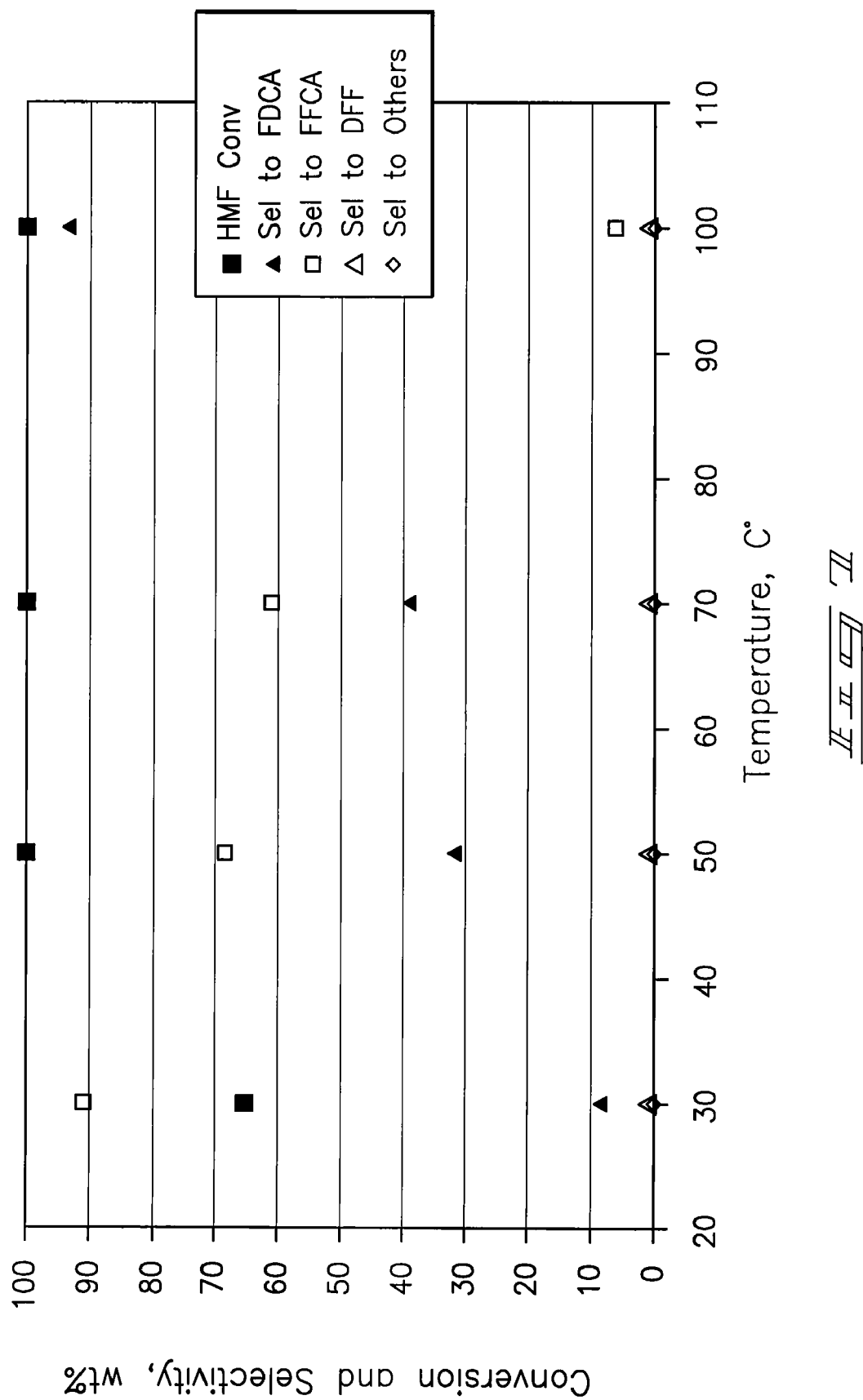
FIG. 7 shows HMF conversion and product selectivity as a function of temperature using the catalyst of FIG. 1. P=150 psig, 0.828% $Na_2CO_3$ added to 1% HMF, LHSV=7.5 $h^{-1}$ air, GHSV=300 $h^{-1}$, data taken at time on stream=140 min.
Figure 8:
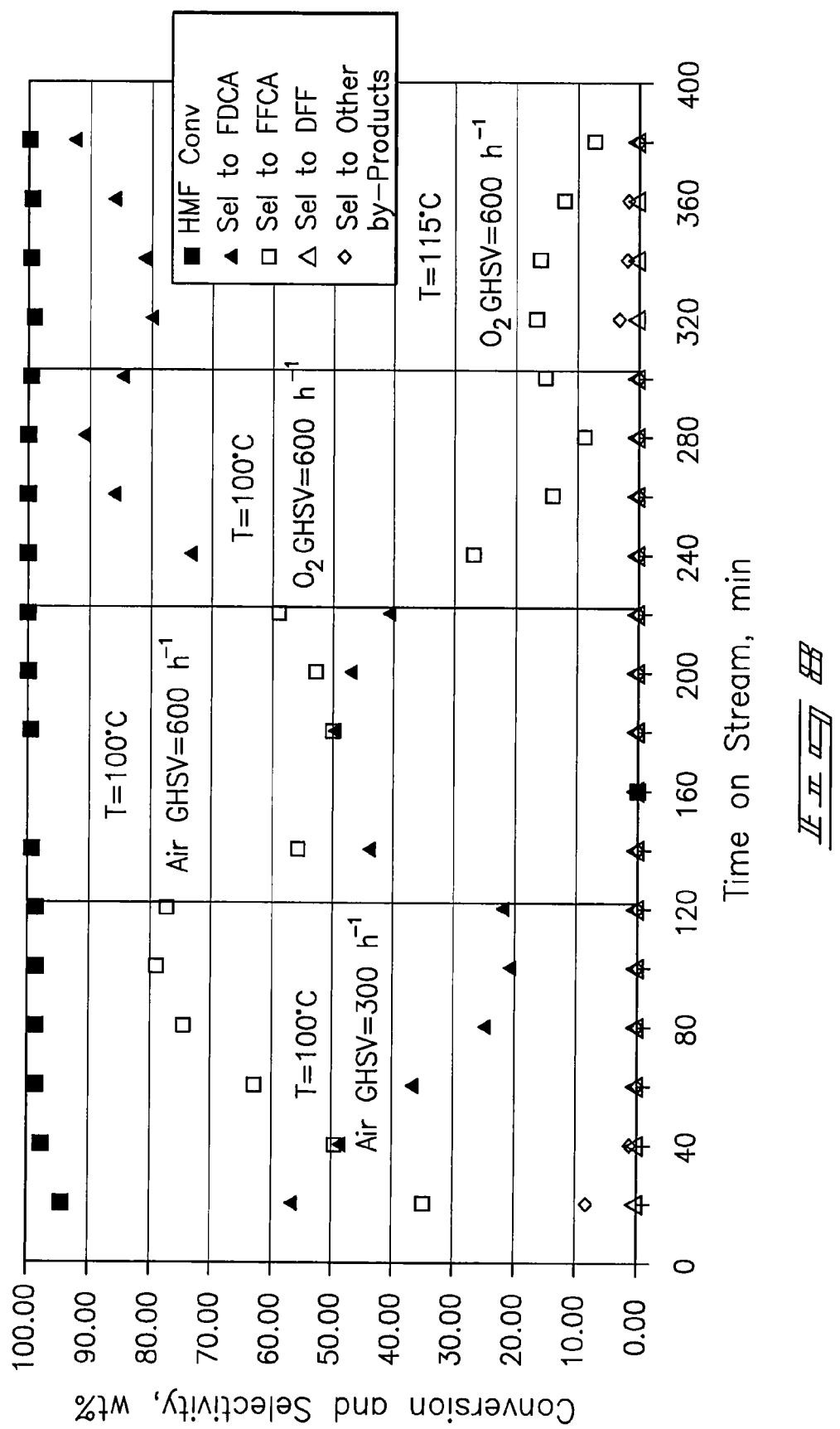
FIG. 8 shows HMF conversion and product selectivity as a function of time on stream utilizing the catalyst of FIG. 1 at the specified temperature and GHSV (either air or $O_2$). P=150 psig, T=100-115° C., 2.486% $Na_2CO_3$ added to 3% HMF LHSV=4.5 $h^{-1}$, air GHSV=300-600 $h^{-1}$ or $O_2$ GHSV=600 $h^{-1}$, catalyst reduced at 30° C. wet.
Figure 9:
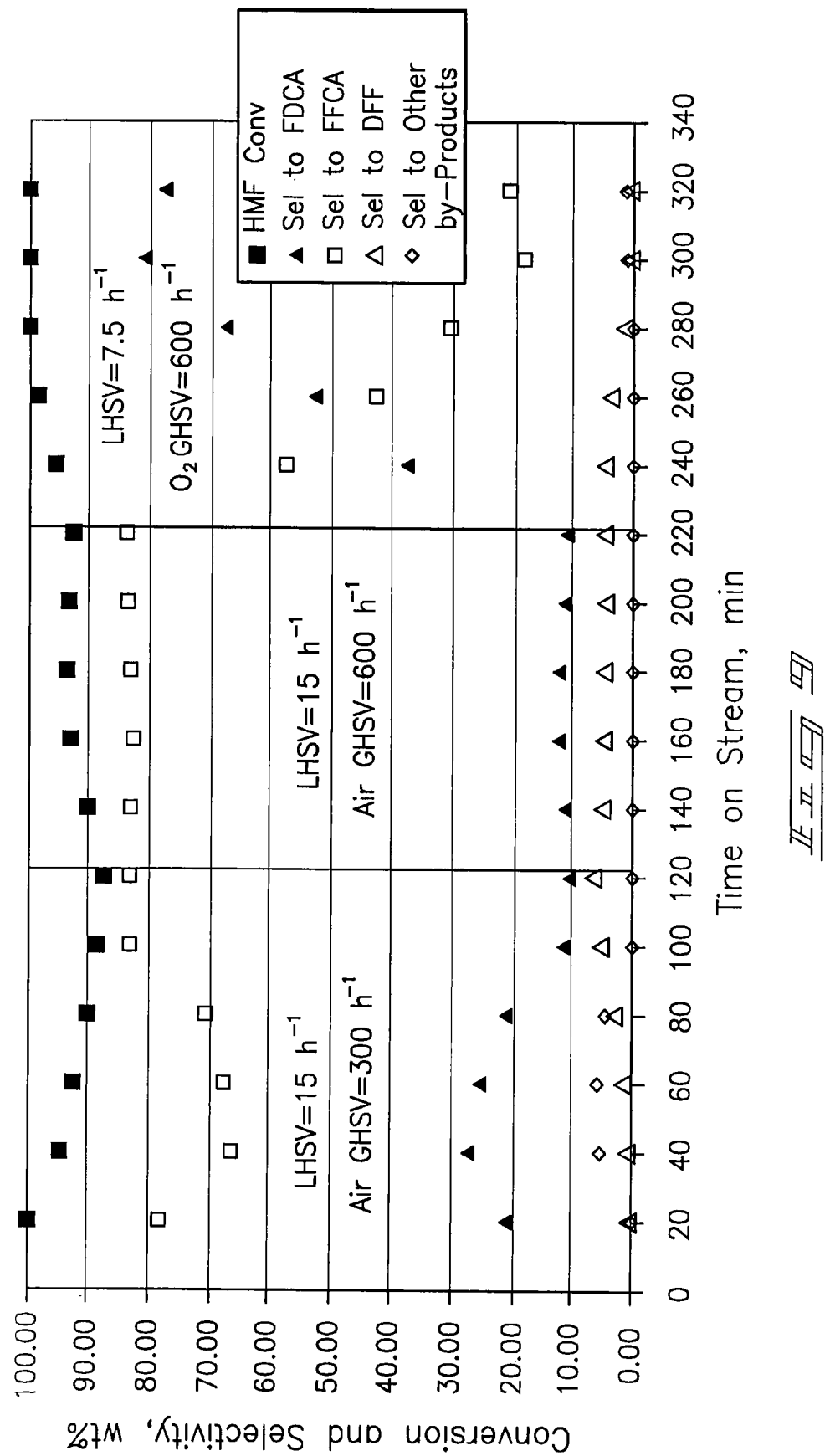
FIG. 9 shows HMF conversion and product selectivity as a function of time on steam utilizing the catalyst of FIG. 1 under air or $O_2$ at varied LHSV and/or GHSV. P=150 psig, T=130° C., 0.828% $Na_2CO_3$ added to 1% HMF, LHSV=7.5-15 $h^{-1}$, air GHSV=300-600 $h^{-1}$ or $O_2$ GHSV=600 $h^{-1}$, catalyst reduced at 30° C. wet.
Figure 11:
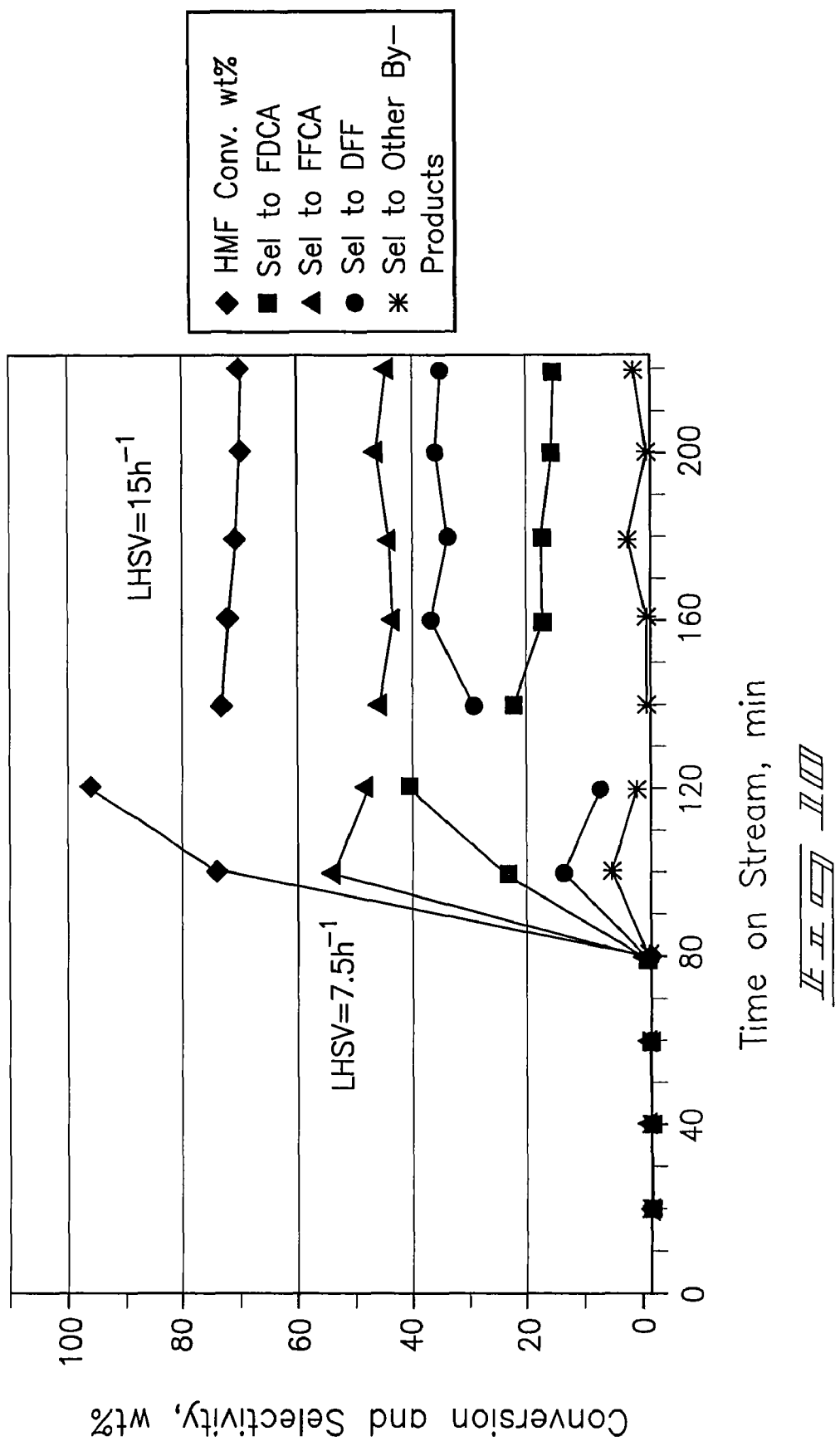
FIG. 11 shows HMF conversion and product selectivity as a function of time on stream utilizing the catalyst of FIG. 1 and the conditions of FIG. 10 with the exception of 0.8% added $Na_2CO_3$.
Figure 11:
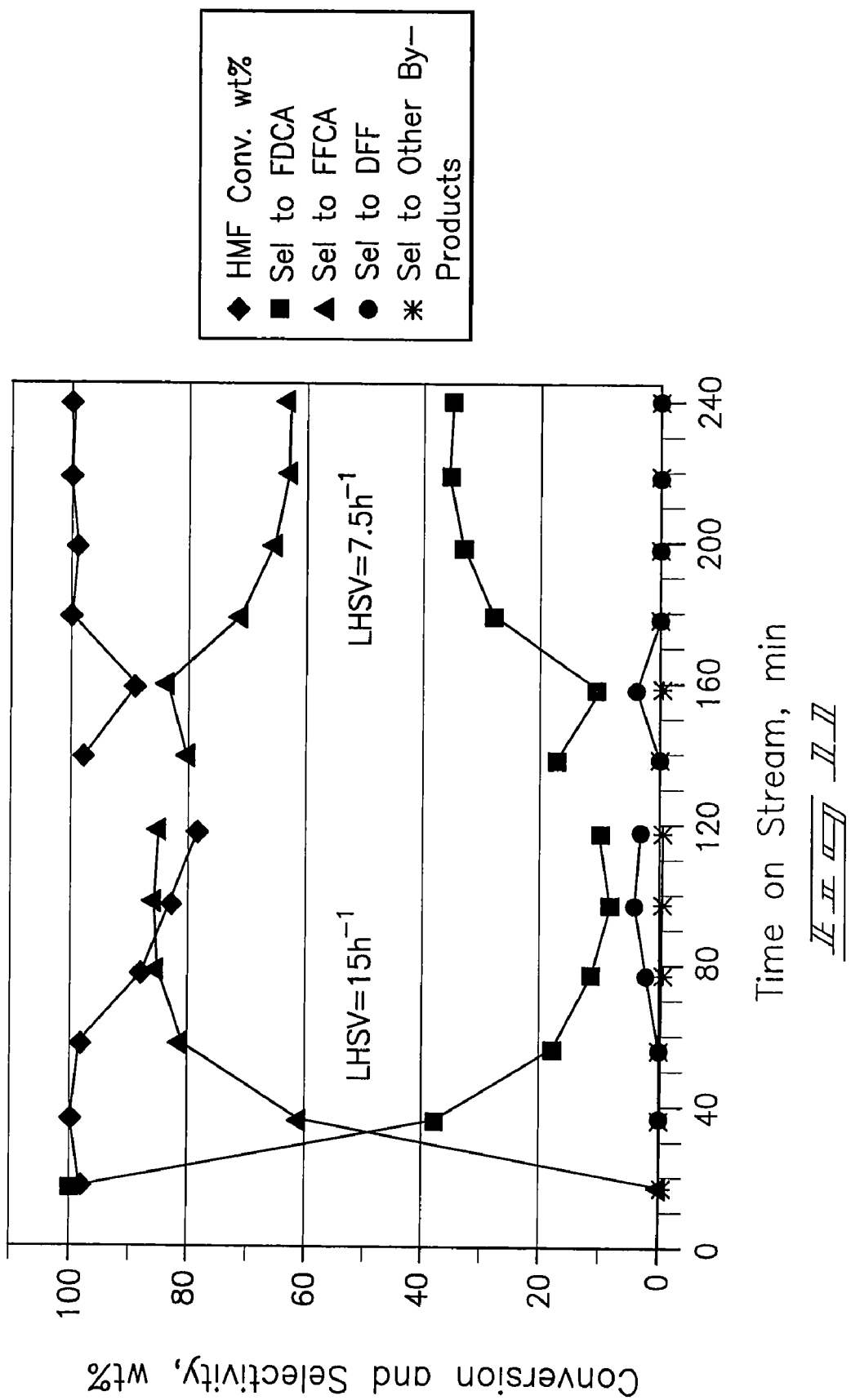
Figure 11:
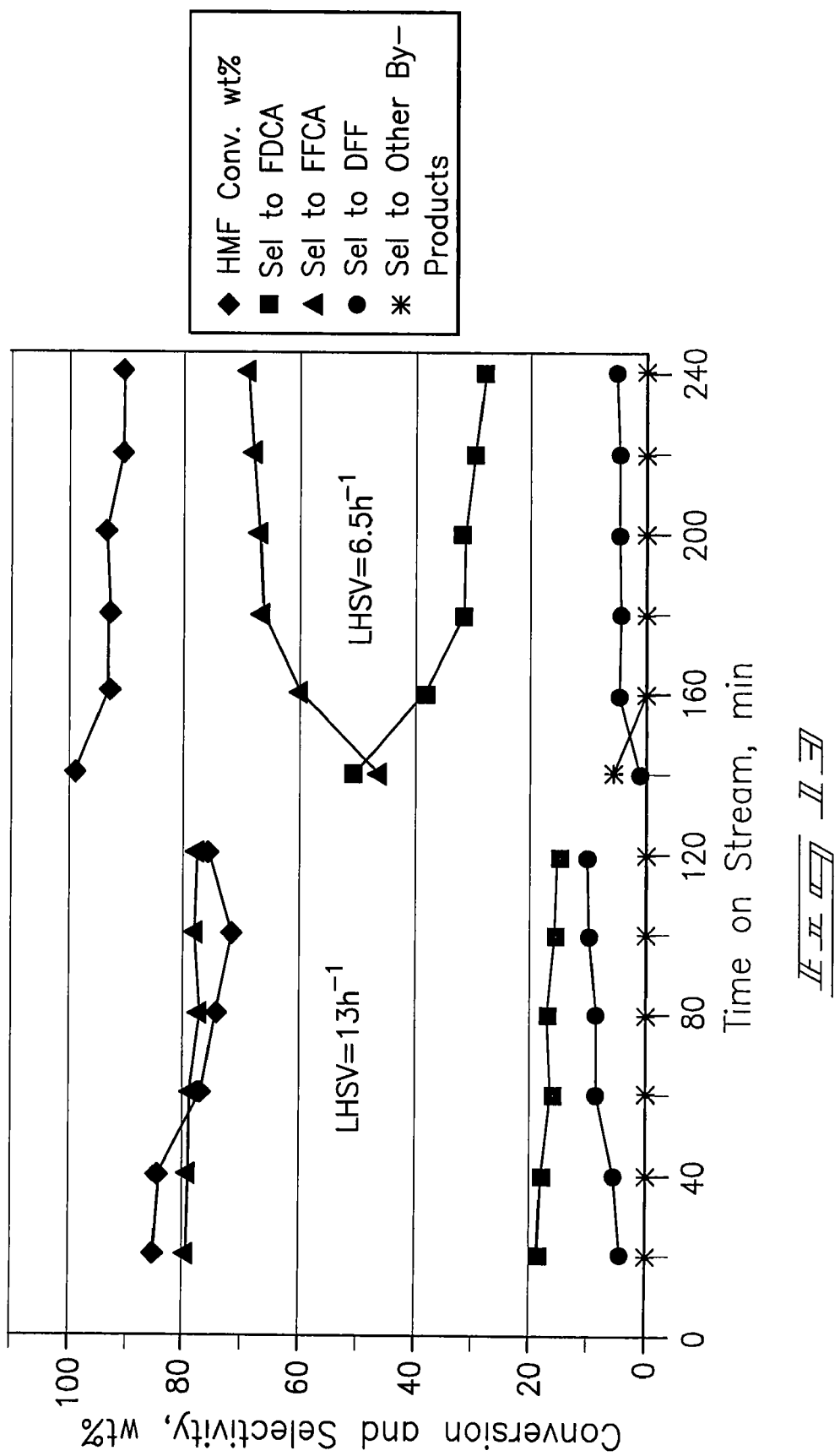
Figure 14:
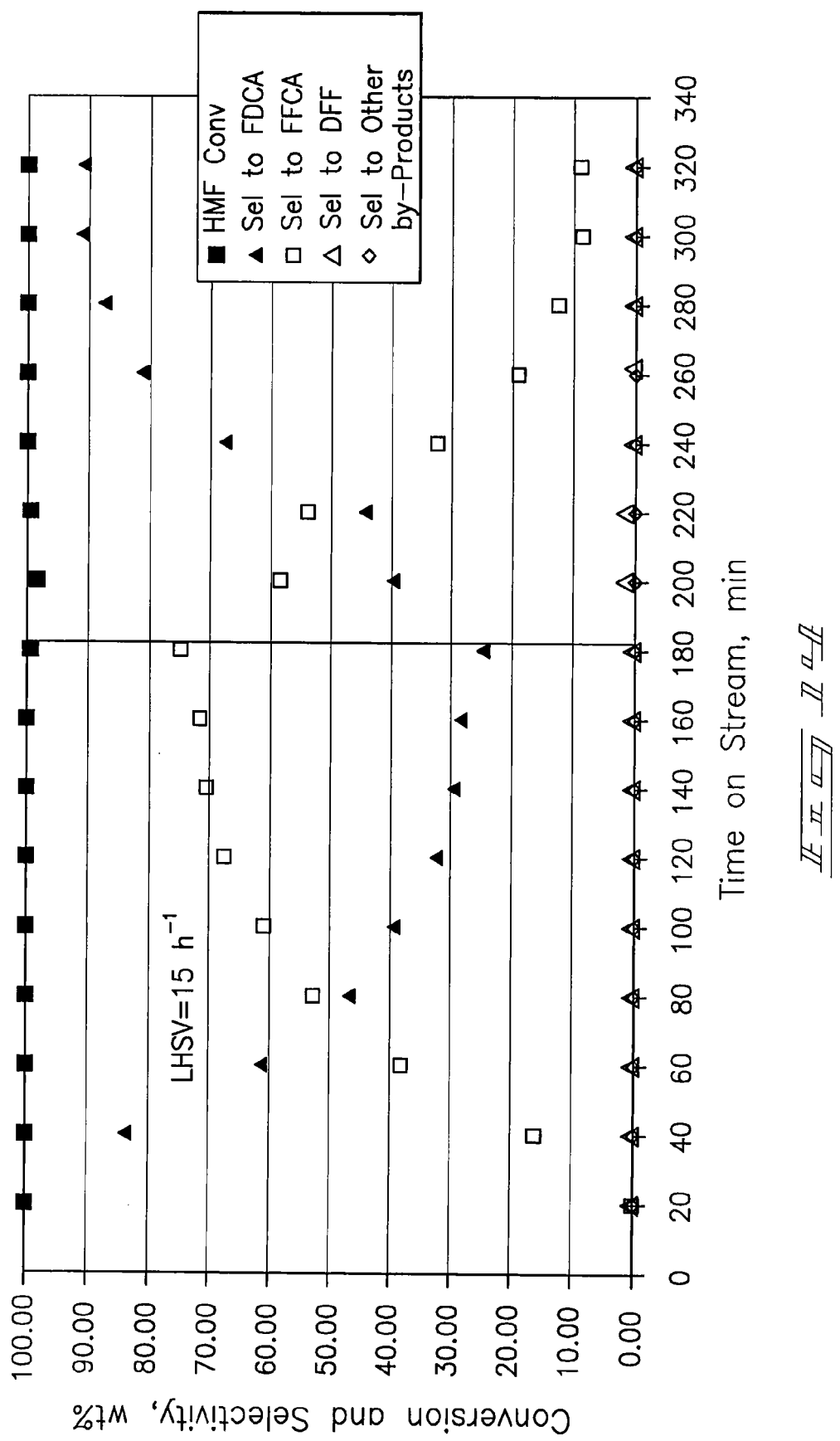
FIG. 14 shows HMF conversion and product selectivity utilizing a 9.65% Pt supported on carbon catalyst. The conditions utilized were P=150 psig, T=100° C., 0.828%
Figure 15:
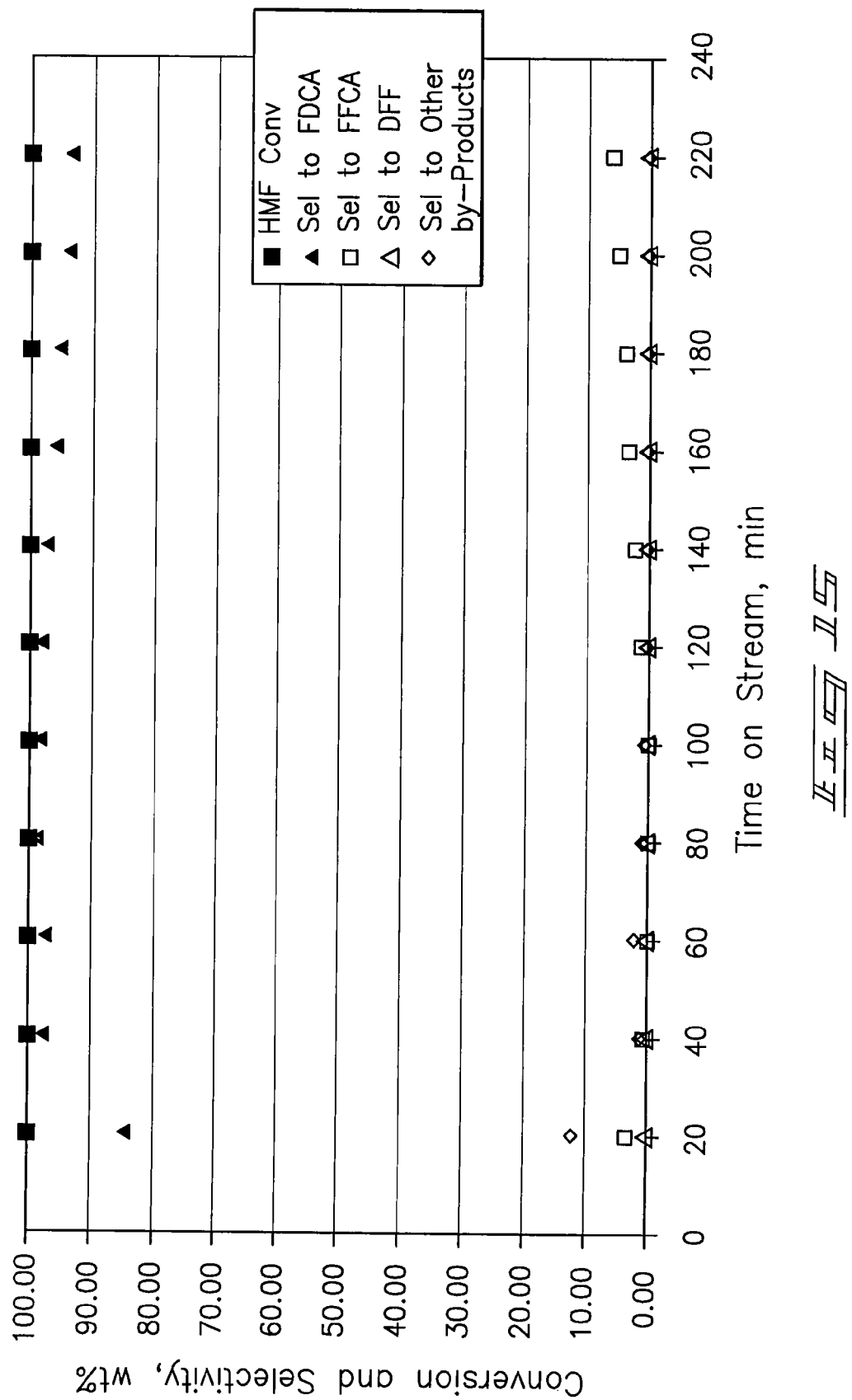

FIG. 15 shows HMF conversion and product selectivity as a function of time on stream utilizing the catalyst of FIG. 14. P=150 psig, T=100° C., 2.414% Na$_2$CO$_3$ added to 3% HMF LHSV=4.5 h$^{-1}$, air GHSV=600 h$^{-1}$, catalyst reduced at 30° C. wet.

Figure 16:
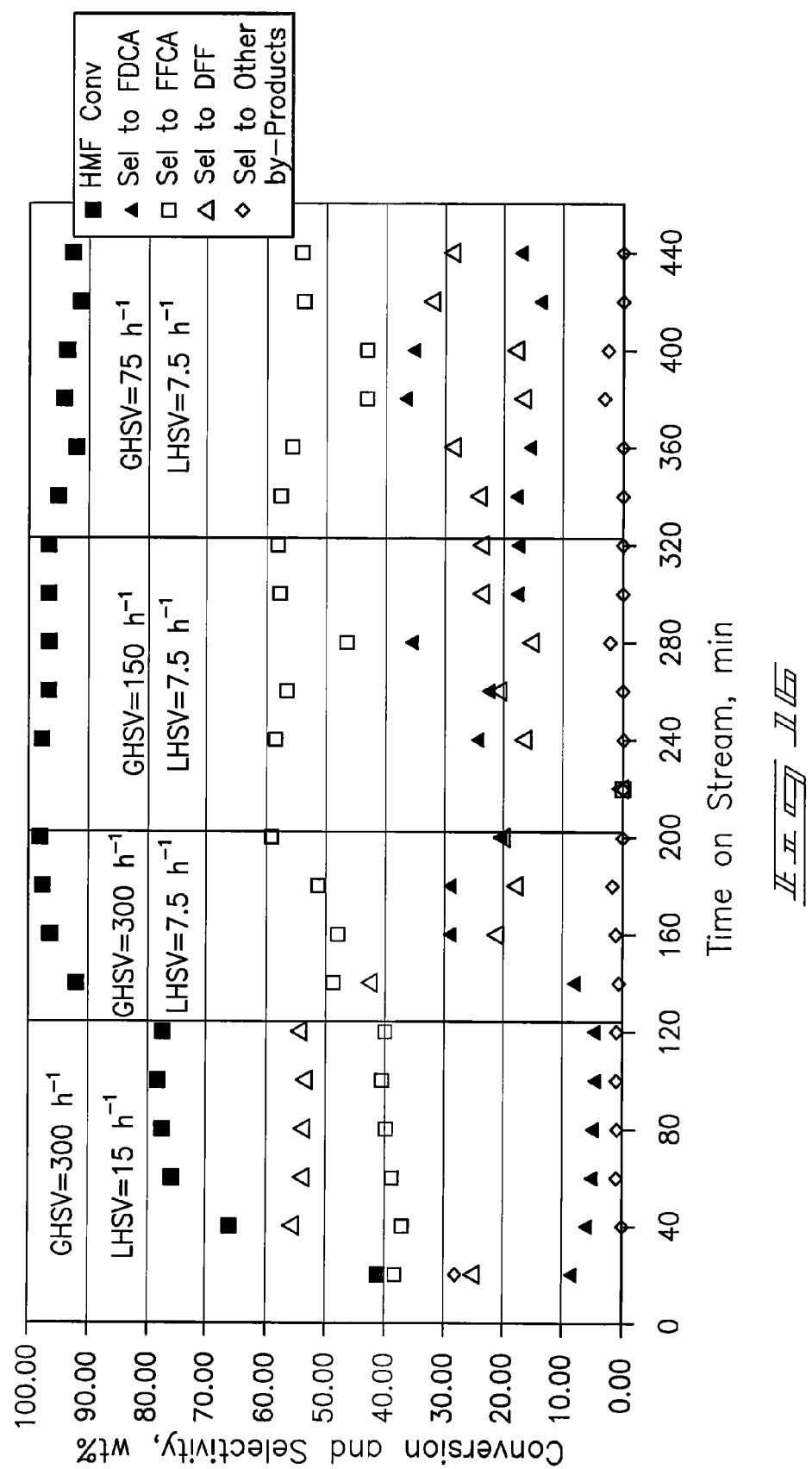

FIG. 16 shows HMF conversion and product selectivity as a function of time on stream for various air GHSV and LHSV. P=150 psig, T=100° C., 1% HMF LHSV=7.5-15 h$^1$, air GHSV=75-300 h$^{-1}$, catalyst reduced at 30° C. wet.

Figure 17:
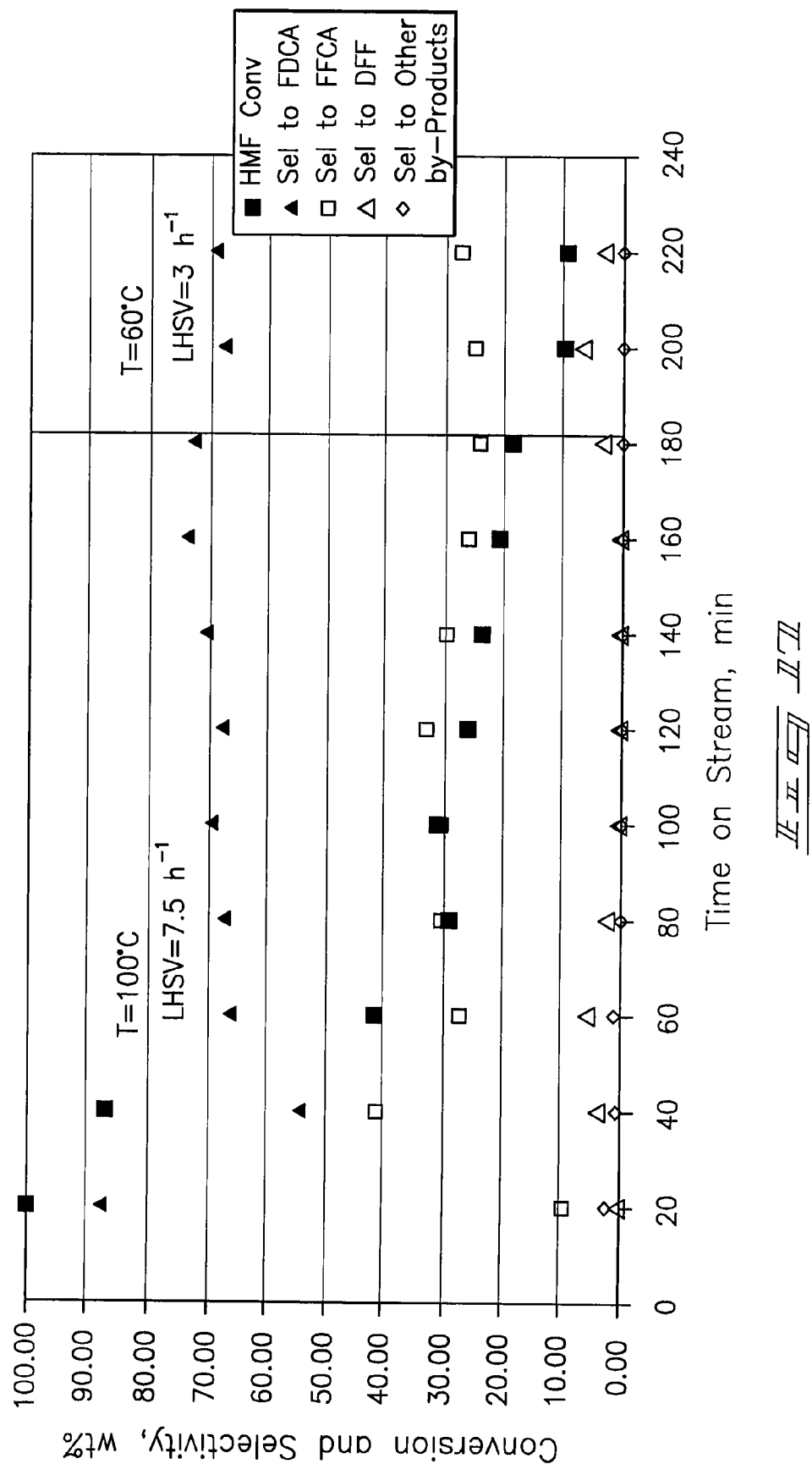

FIG. 17 shows HMF conversion and product selectivity as a function of time on stream utilizing the catalyst of FIG. 14 at varied temperature and LHSV. P=150 psig, T=60-100° C., 1% HMF LHSV=3-7.5 h$^1$, 1% O$_2$ diluted air GHSV=300 h$^1$, catalyst reduced at 30° C. wet.

Figure 18B:
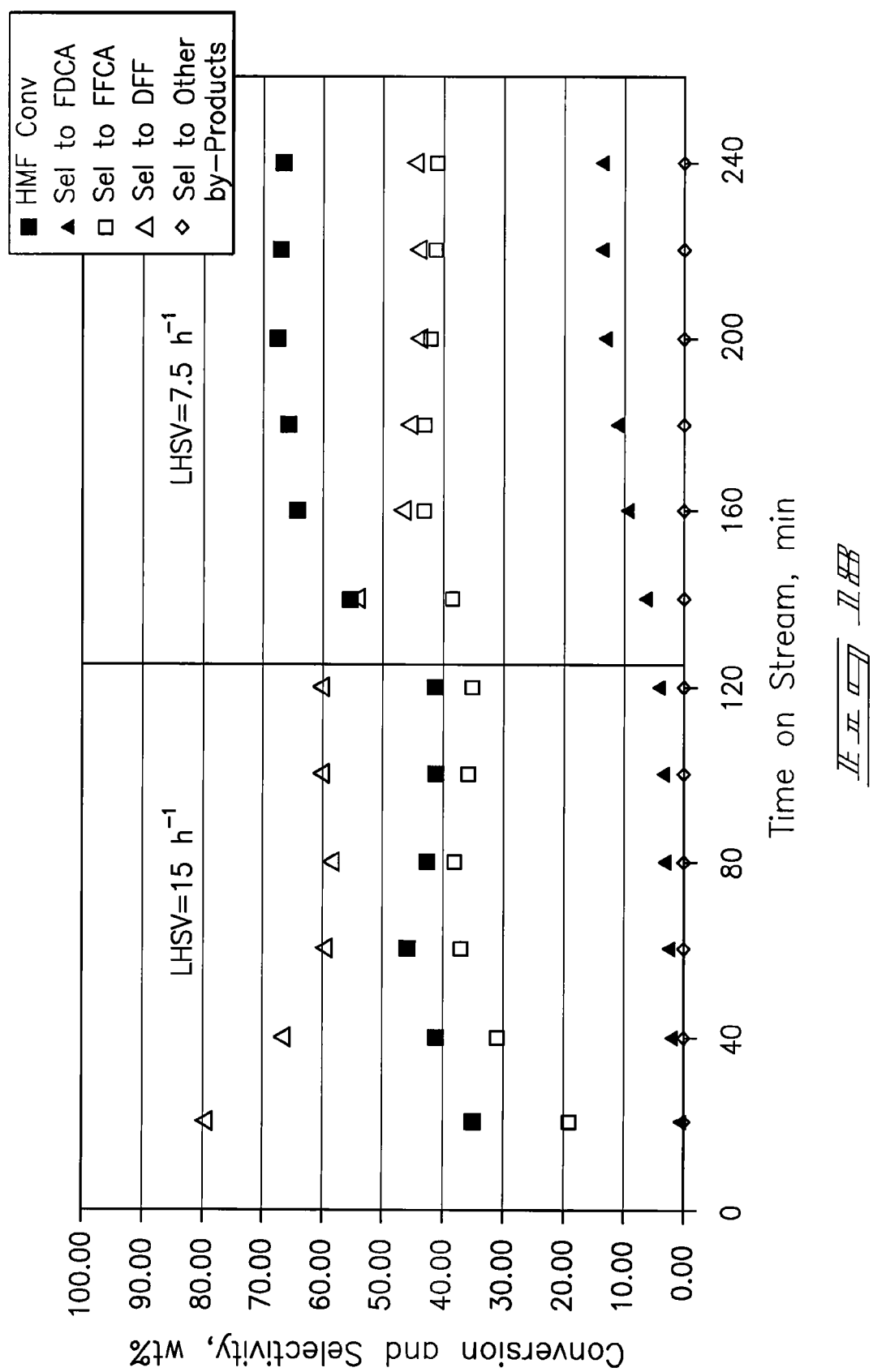

FIG. 18 shows HMF conversion and selective product production utilizing a 5% Pt on an Al$_2$O$_3$ support catalyst as a function on time on stream at varied LHSV. P=150 psig, T=100° C., 1% HMF LHSV=15-7.5 h$^{-1}$, air GHSV=300 h$^{-1}$, catalyst reduced at 30° C. wet.

Figure 19:
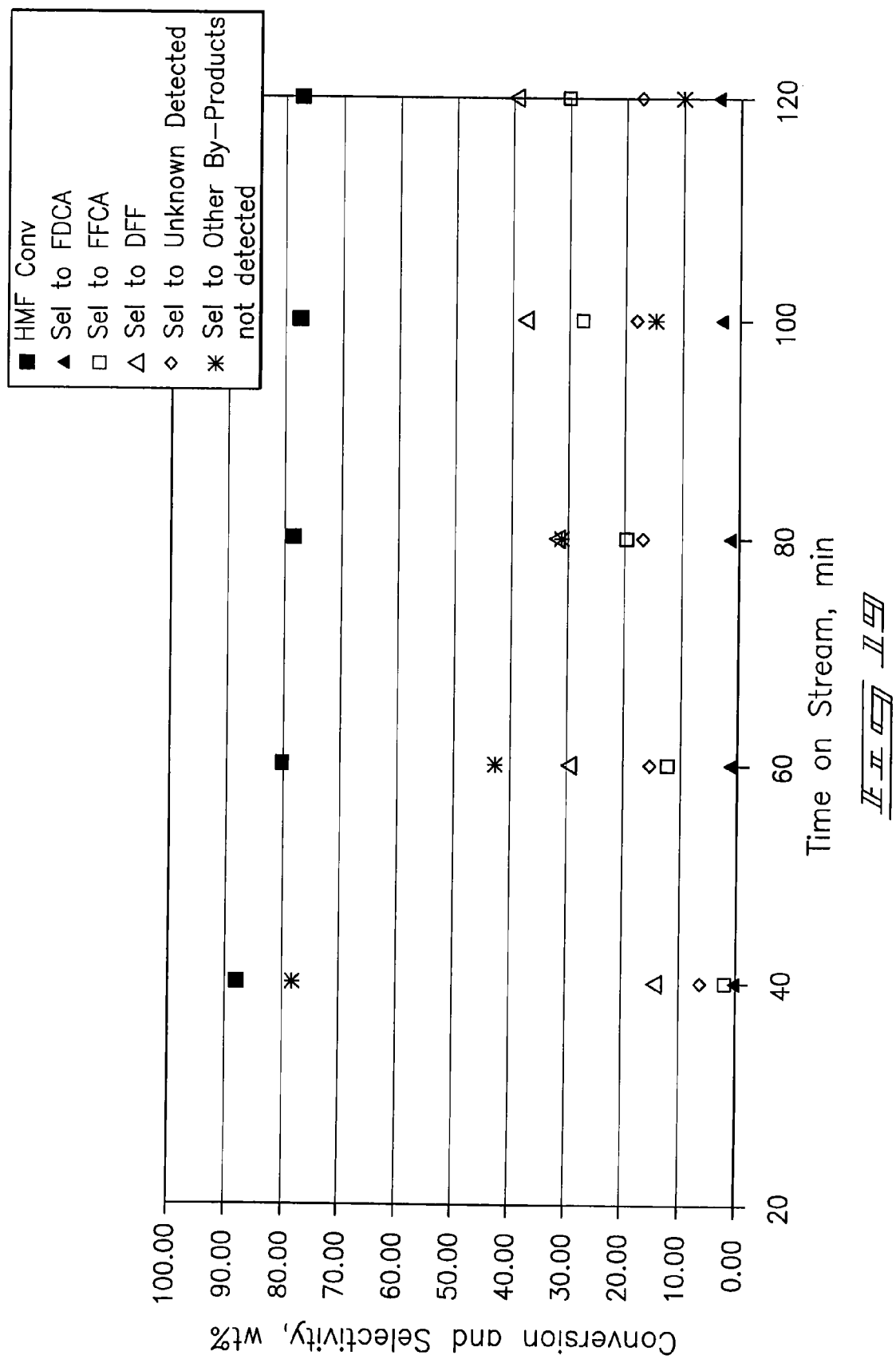

FIG. 19 shows HMF conversion and product selectivity as a function of time on stream utilizing the catalyst FIG. 18 at an increased temperature (130° C.) relative to FIG. 18. P=150 psig, 1% HMF LHSV=7.5 h$^{-1}$, air GHSV=300 h$^{-1}$, catalyst reduced at 30° C. wet.

Figure 20:
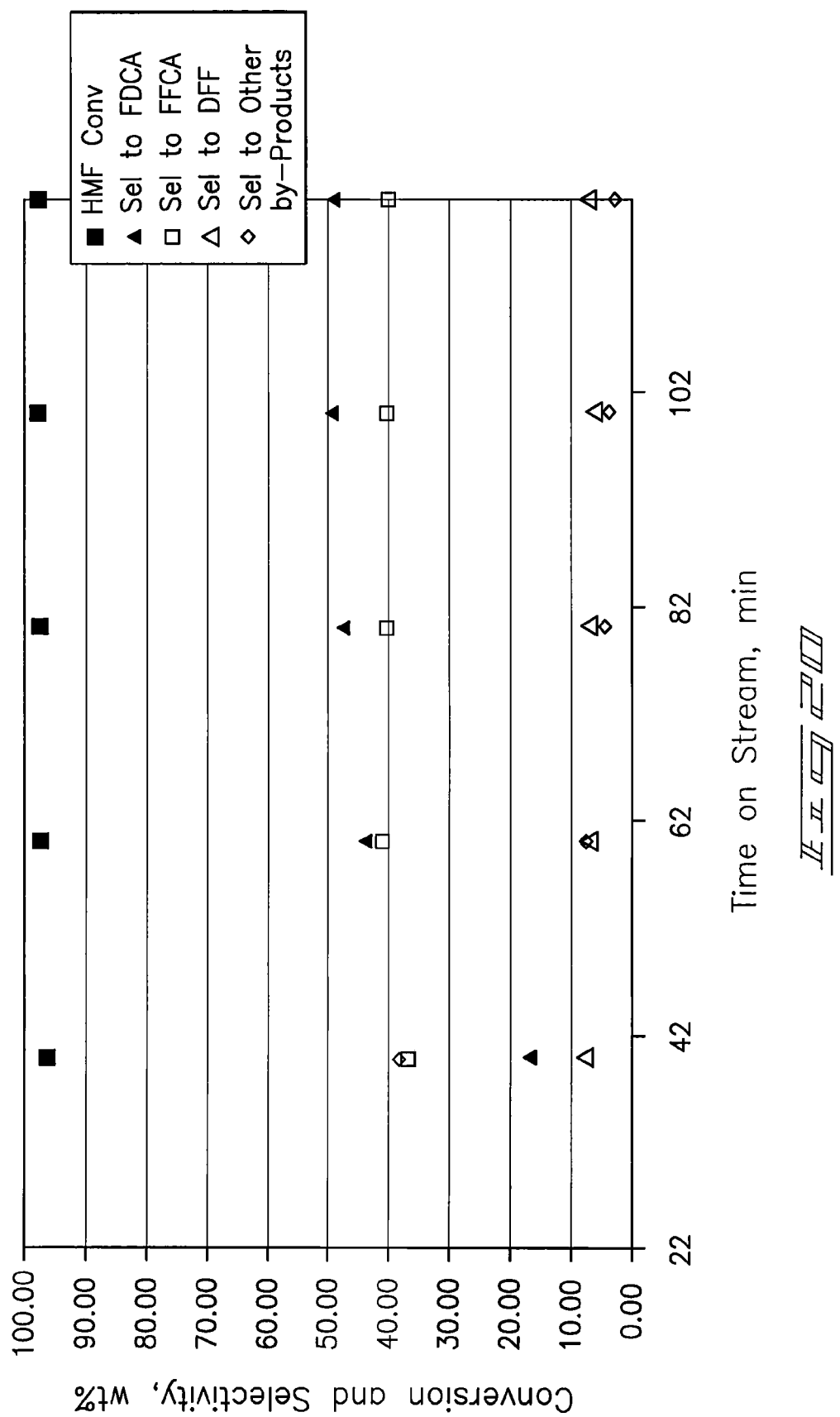

FIG. 20 shows HMF conversion and product selectivity as a function of time on stream utilizing the catalyst of FIG. 18 in the presence of O$_2$. P=150 psig, T=100° C., 1% HMF LHSV=7.5 h$^{-1}$, 100% O$_2$ GHSV=300 h$^{-1}$, catalyst reduced at 30° C. wet.

Figure 21:
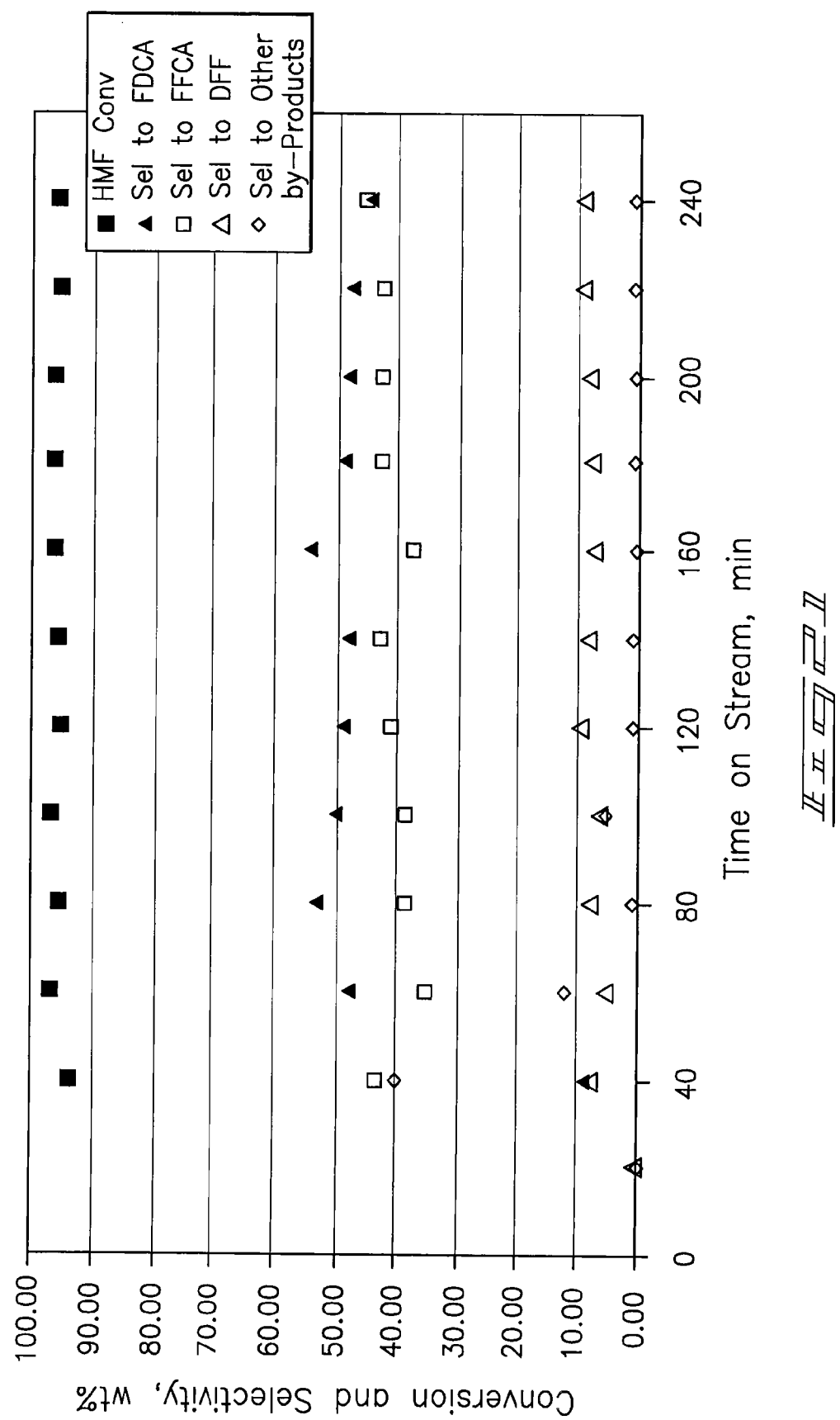

FIG. 21 shows HMF conversion and product selectivity as a function of time on stream utilizing the catalyst of FIG. 18 and the conditions of FIG. 20 with the exception that P=300 psig.

Figure 22:
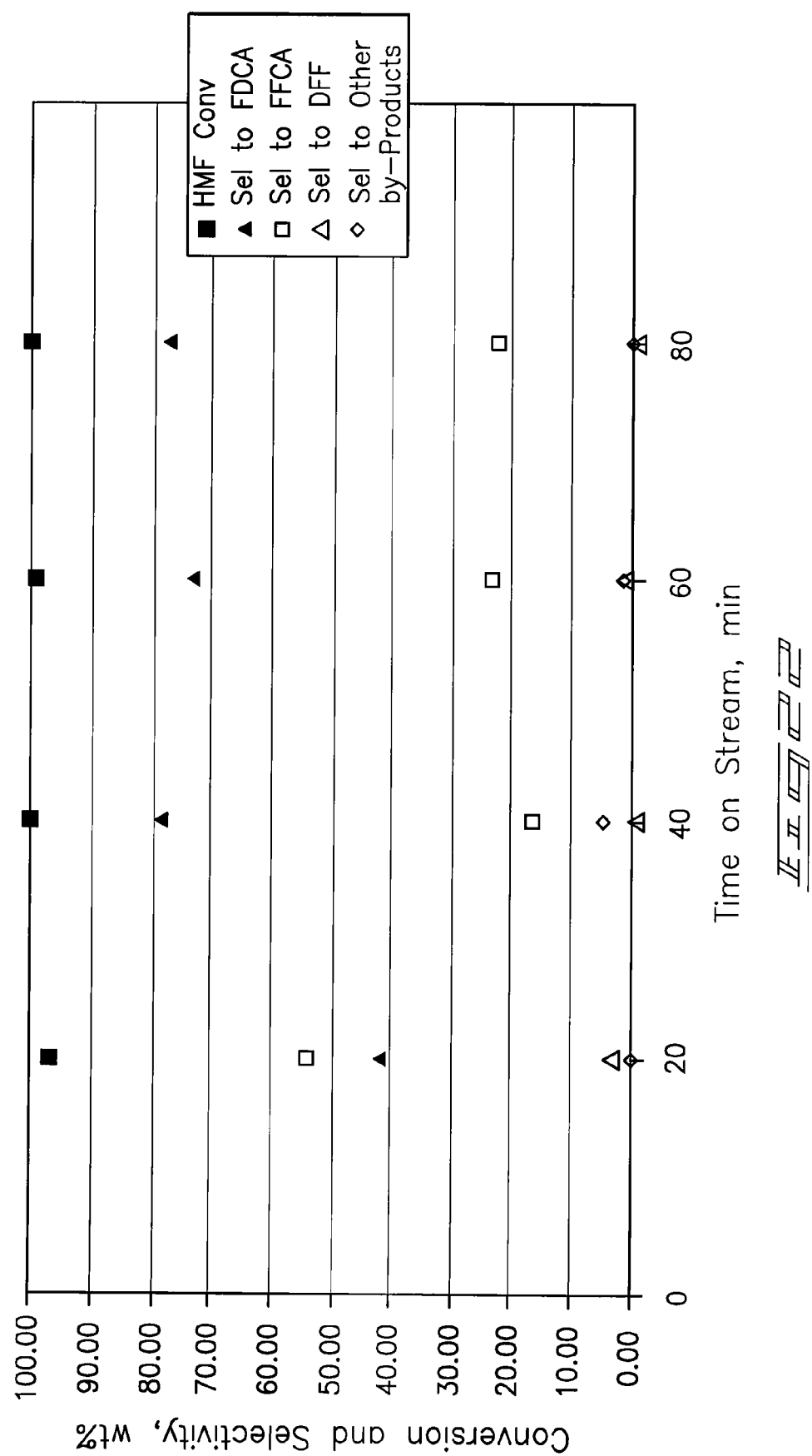

FIG. 22 shows HMF conversion and product selectivity as a function of time on stream utilizing the catalyst of FIG. 18 and the conditions of FIG. 20 with the exception that 100% O$_2$ GHSV=600 h$^{-1}$.

Figure 23:
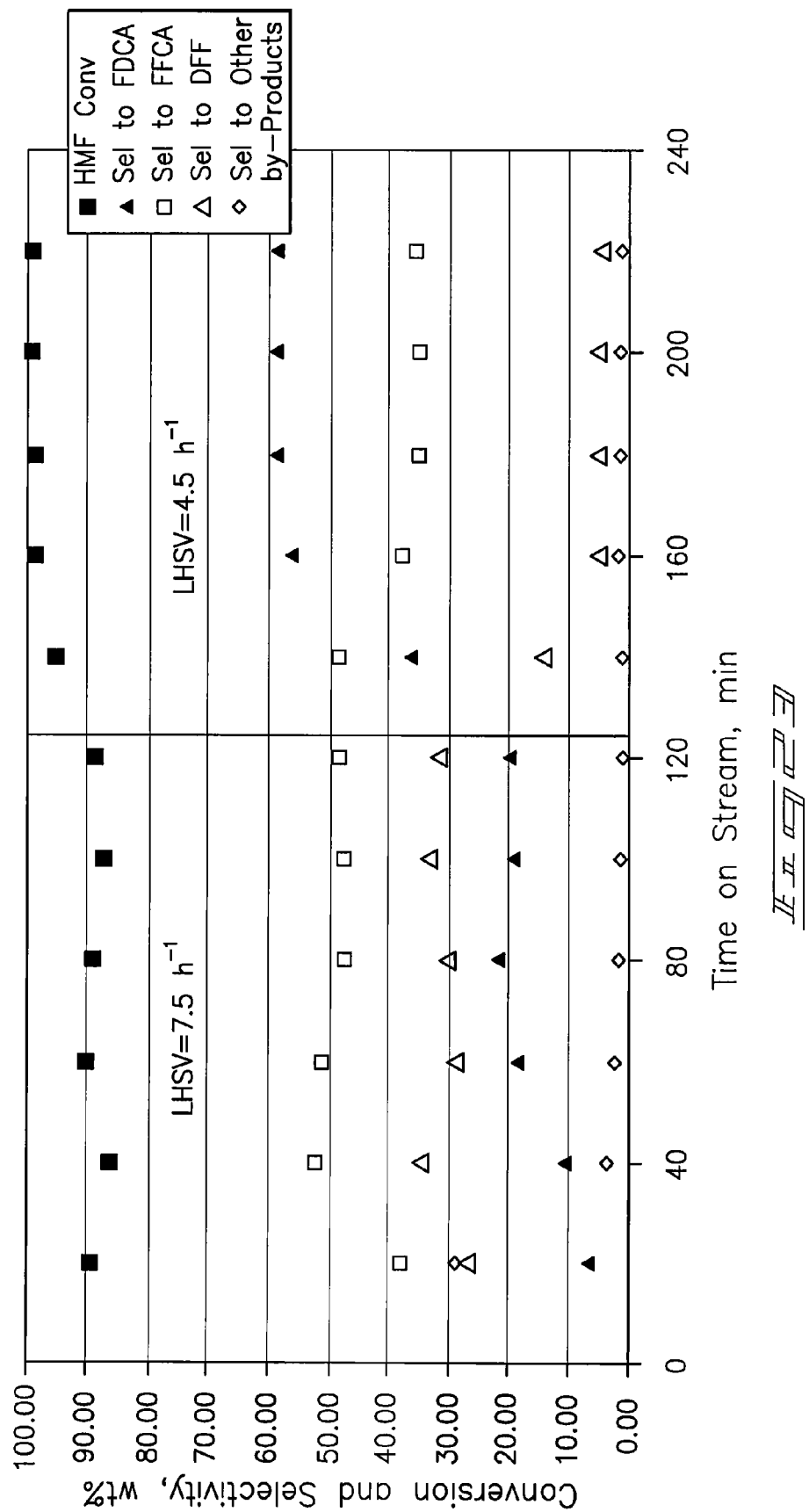

FIG. 23 shows HMF conversion and product selectivity as a function of time on stream utilizing the catalyst of FIG. 18 at varied LHSV. P=150 psig, T=100° C., 1% HMF LHSV=7.5-4.5 h$^{-1}$, air GHSV=600 h$^{-1}$, catalyst reduced at 30° C. wet.

Figure 24:
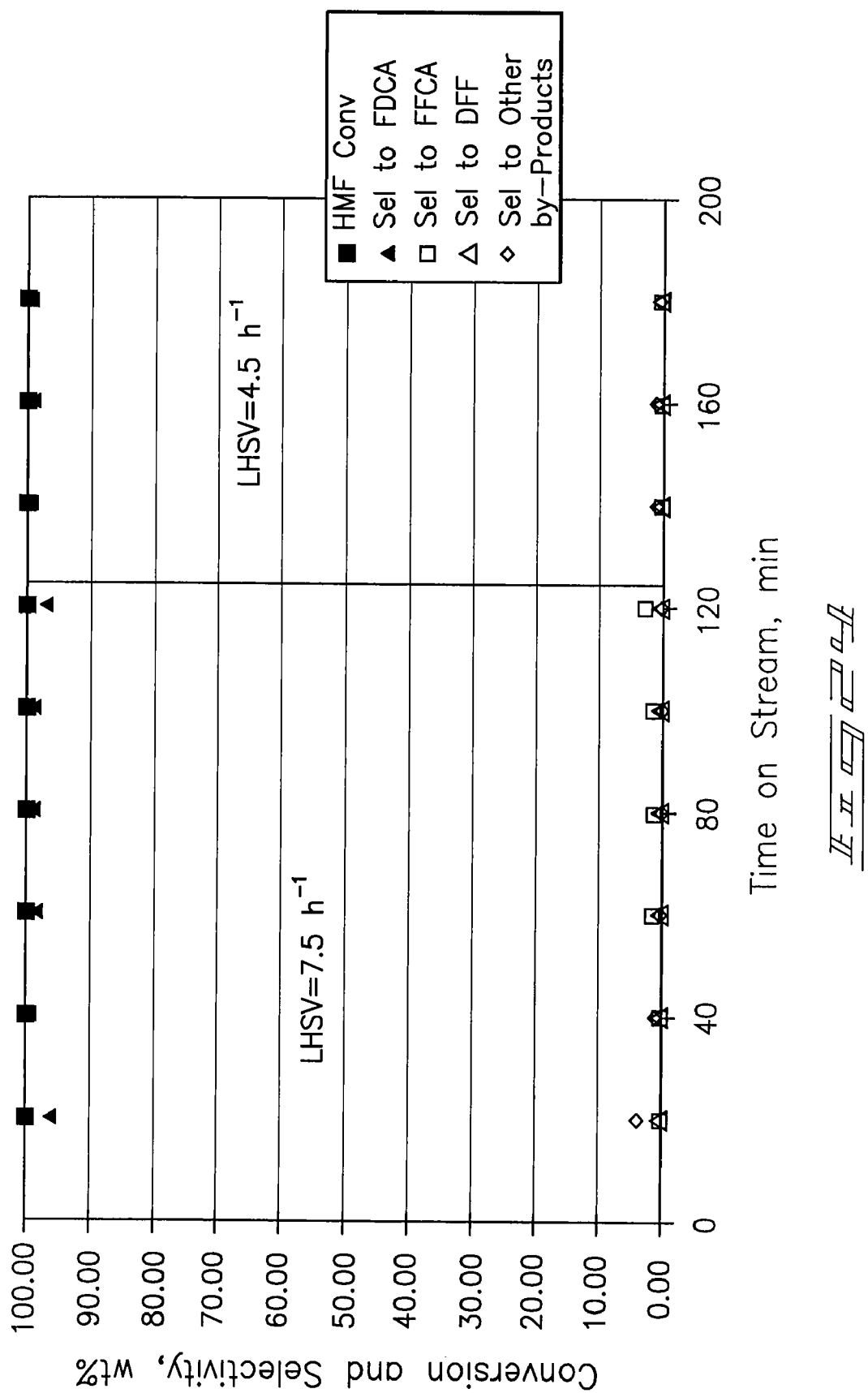

FIG. 24 shows HMF conversion and product selectivity as a function of time on stream utilizing the catalyst of FIG. 18 at varied LHSV in the presence of O$_2$. P=150 psig, T=100° C., 0.828 weight % Na$_2$CO$_3$ added to 1% HMF LHSV=7.5-4.5 h$^{-1}$, O$_2$ GHSV=300 h$^{-1}$, catalyst reduced at 30° C. wet.

Figure 25:
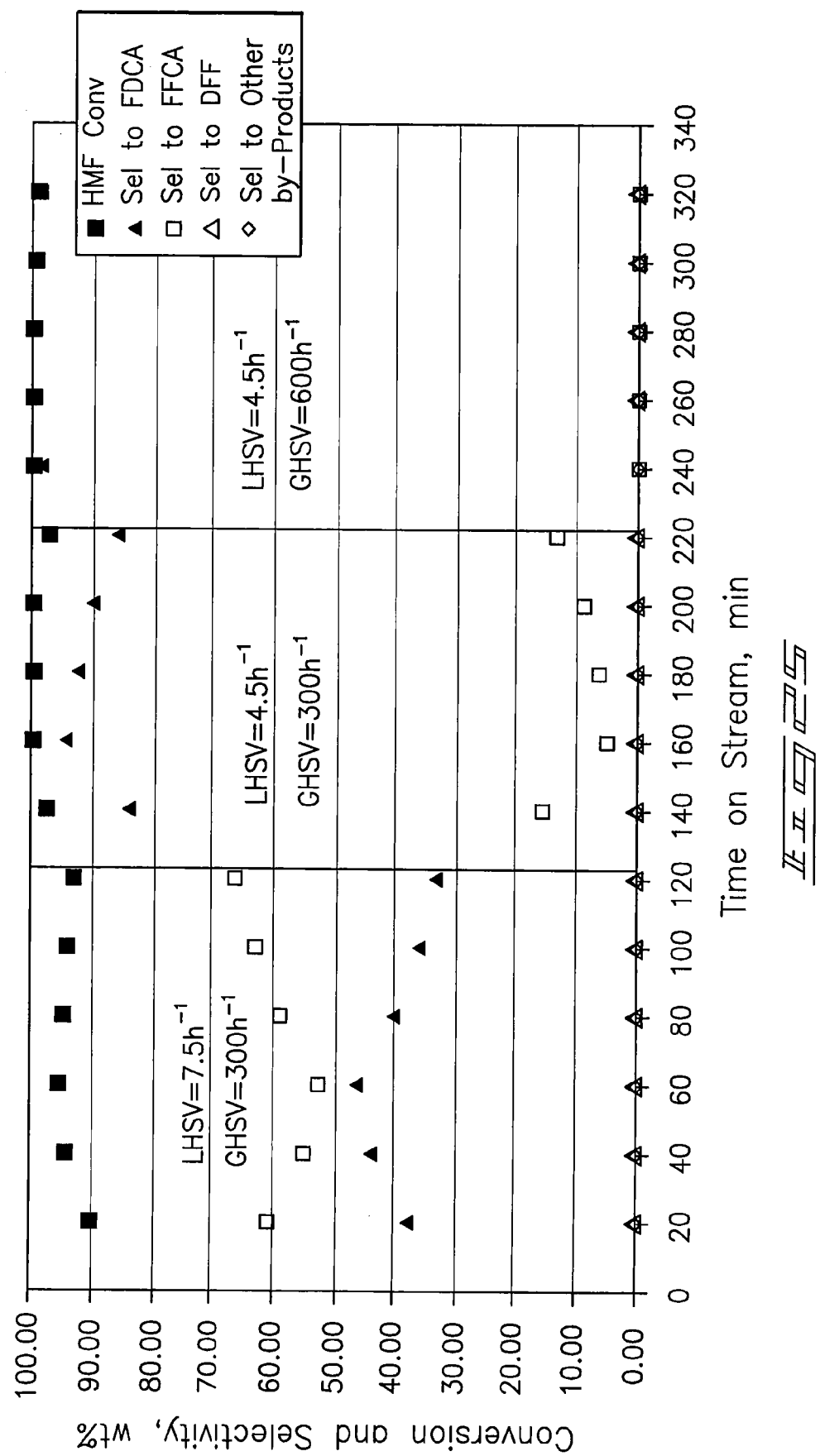

FIG. 25 shows HMF conversion and product selectivity as a function of time on stream utilizing the catalyst of FIG. 18 at varied LHSV and GHSV. P=150 psig, T=100° C., 0.828% Na$_2$CO$_3$ added to 1% HMF LHSV=4.5-7.5 h$^{-1}$, air GHSV=300-600 h$^{-1}$, catalyst reduced at 30° C. wet.

Figure 26:
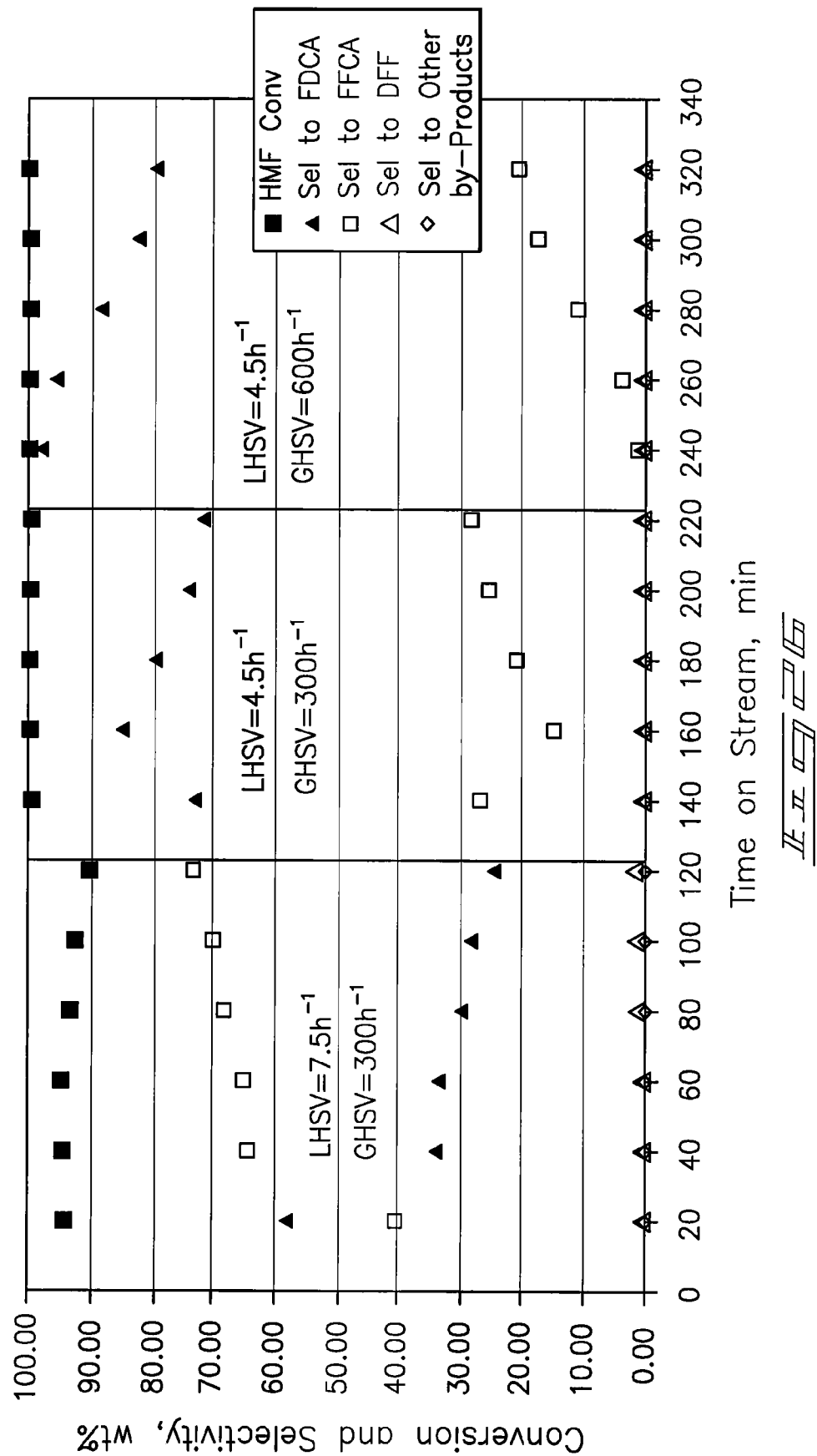

FIG. 26 shows HMF conversion and product selectivity as a function of time on stream utilizing the catalyst of FIG. 18 at varied LHSV and GHSV. P=150 psig, T=70° C., 0.828% Na$_2$CO$_3$ added to 1% HMF LHSV=4.5-7.5 h$^{-1}$, air GHSV=300-600 h$^{-1}$, catalyst reduced at 30° C. wet.

Figure 27:
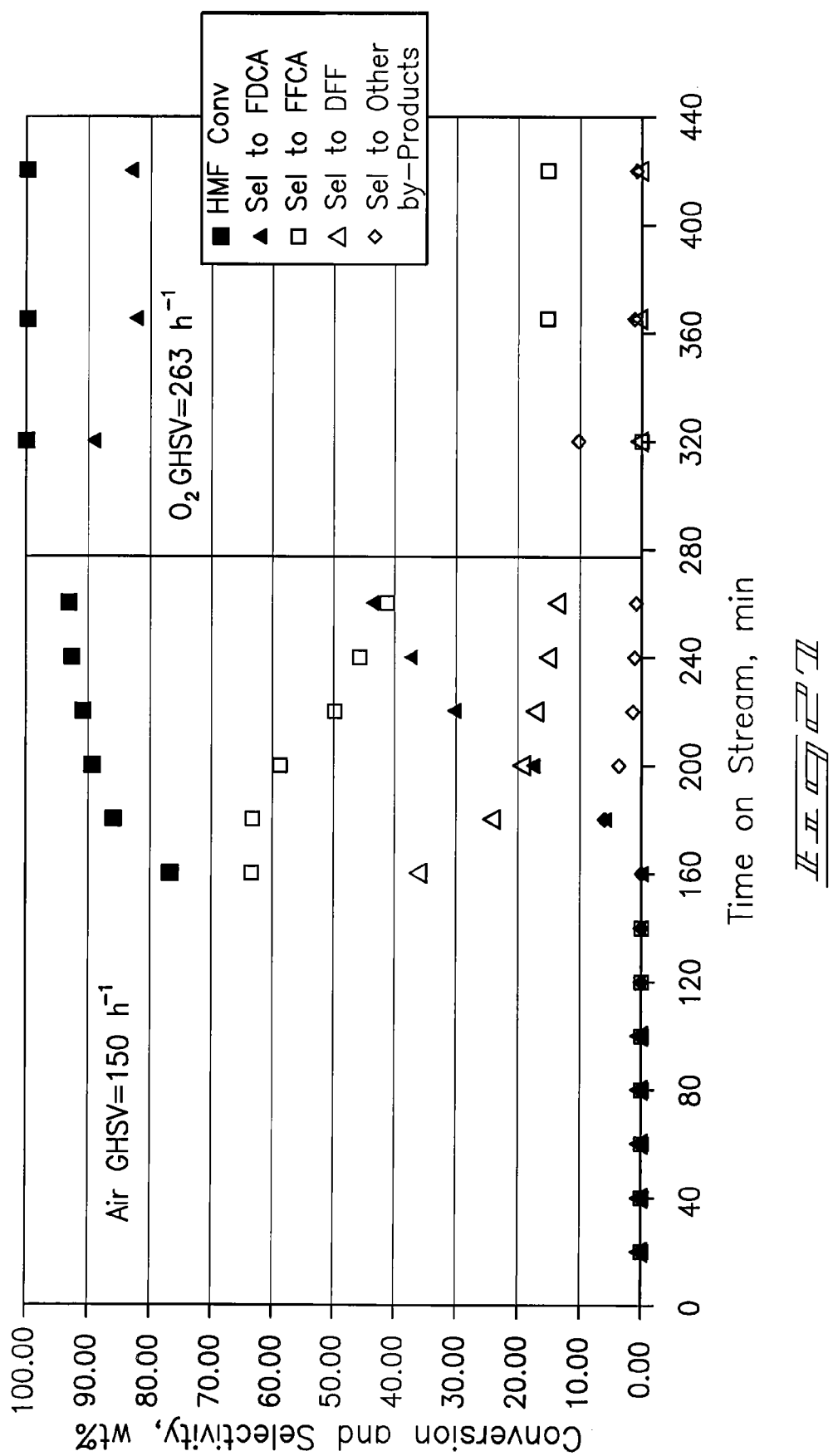

FIG. 27 shows HMF conversion and product selectivity as a function of time on stream utilizing the catalyst of FIG. 18 in an 8 mL catalyst bed in the presence of air and then O$_2$. P=150 psig, T=100° C., 0.5% HMF LSHV=3.75 h$^{-1}$, air then O$_2$ GHSV=150-263 h$^{-1}$, catalyst reduced at 30° C. wet.

Figure 28:
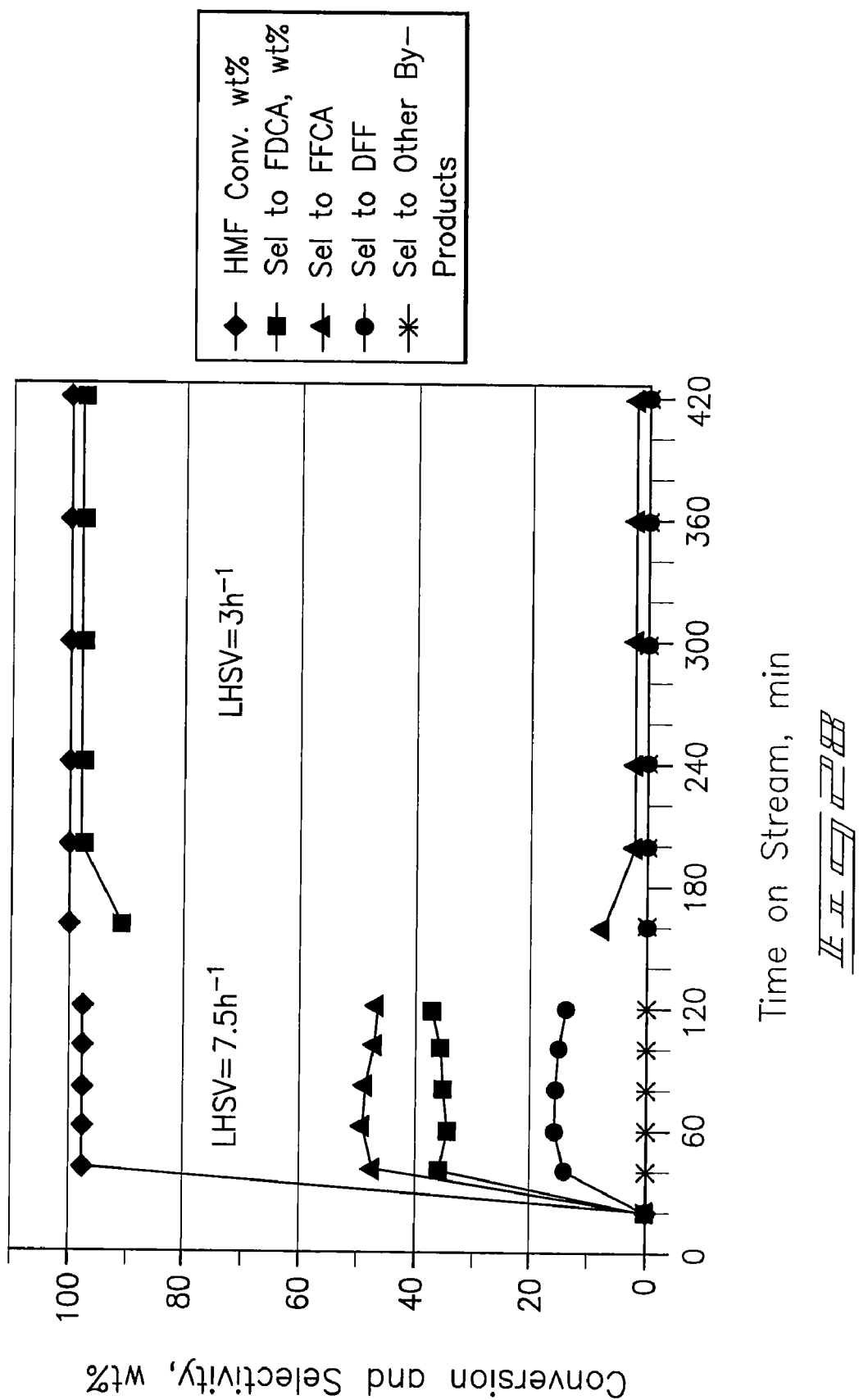

FIG. 28 shows HMF conversion and selective product production as a function of time on stream utilizing a 5% Pt on a ZrO$_2$ support catalyst at varied LHSV in a continuous flow reactor. P=150 psig air, T=100° C. 0.5% HMF LHSV=7.5-3 h$^{-1}$, GHSV=300 h$^{-1}$.

Figure 29:
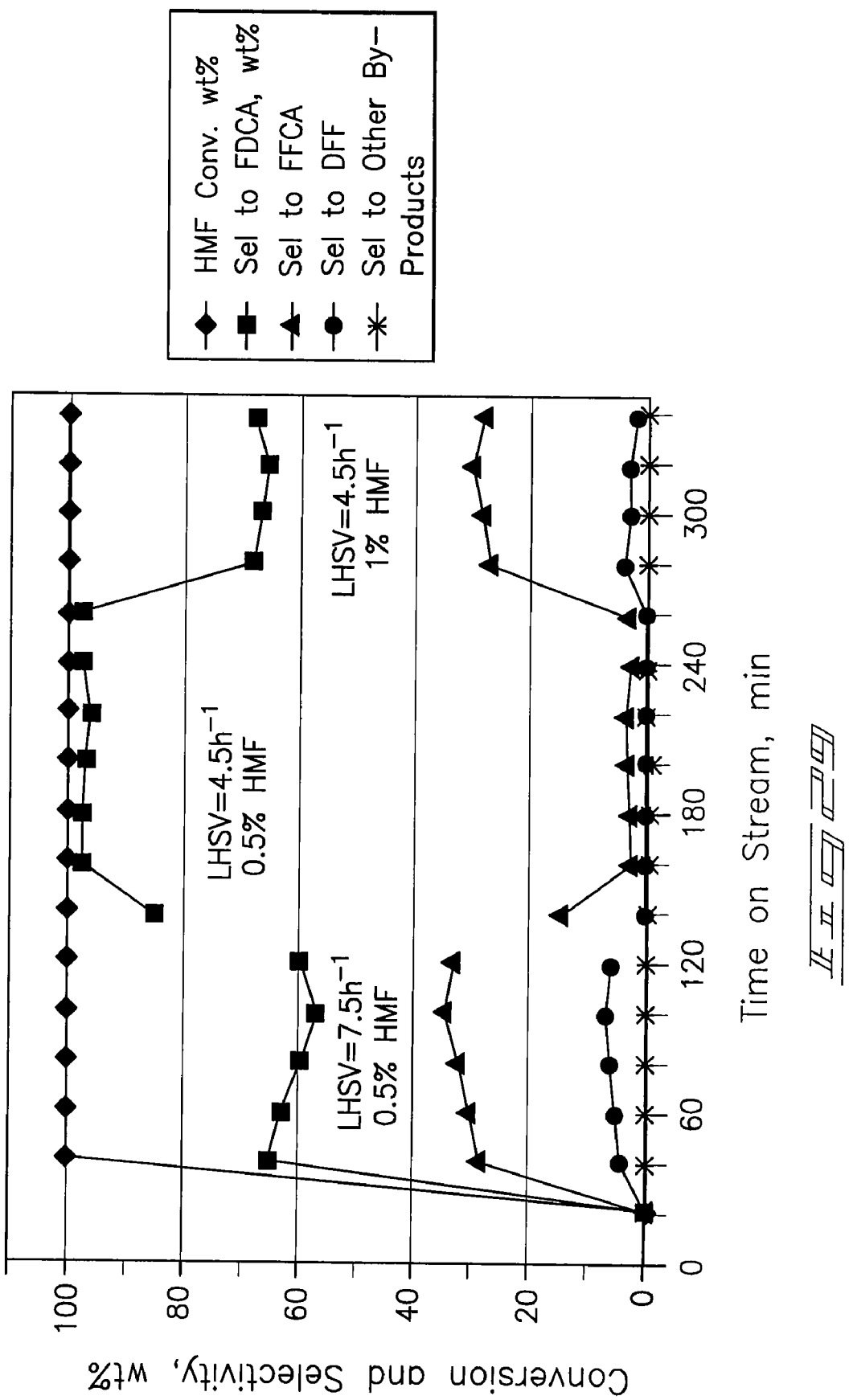

FIG. 29 shows HMF conversion and product selectivity as a function of time on stream utilizing the catalyst of FIG. 28 at varied LHSV and HMF concentration. HMF=0.5-1%, P=150 psig air, T=120° C., LHSV=7.5-4.5 h$^{-1}$, GHSV=300 h$^{-1}$.

Figure 30:
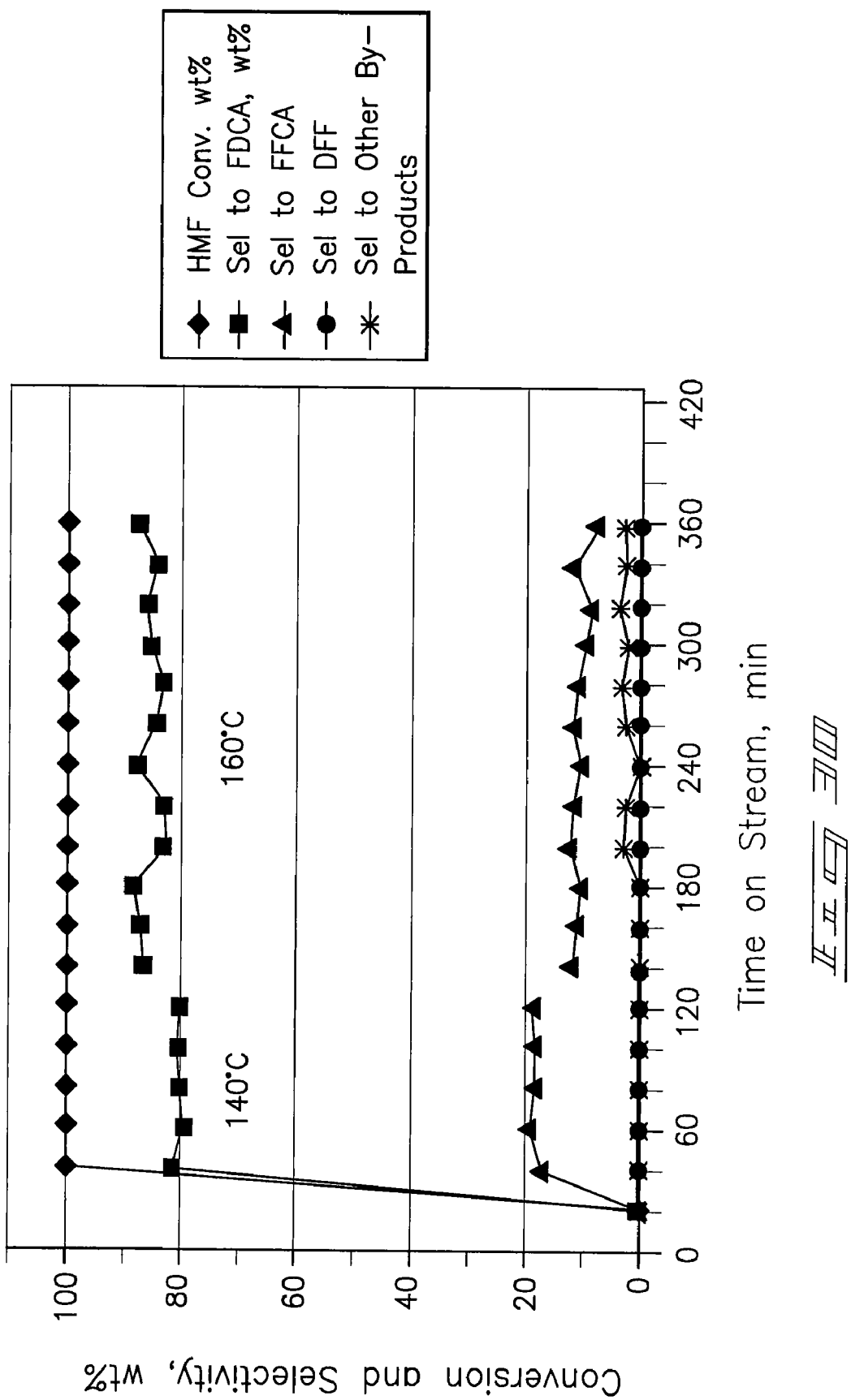

FIG. 30 shows HMF conversion and product selectivity as a function of time on stream utilizing the catalyst of FIG. 28 at varied temperature. P=150 psig air, T=140-160° C., 0.5% HMF LHSV=7.5 h$^{-1}$, GHSV=300 h$^{-1}$.

Figure 31:
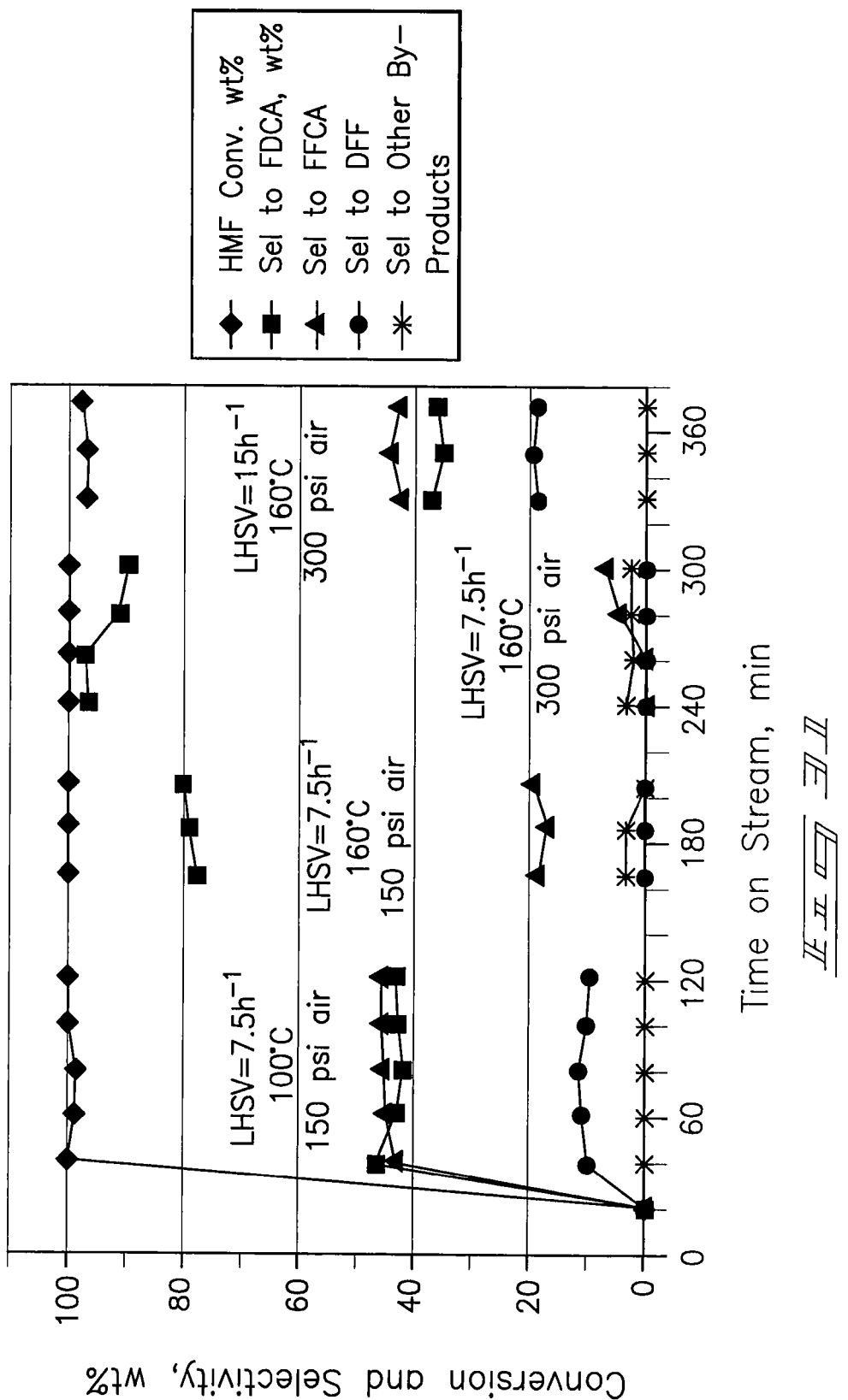

FIG. 31 shows HMF conversion and product selectivity as a function of time on stream utilizing the catalyst of FIG. 28 at varied LHSV at varied temperature and at varied psi air. P=150-300 psig air, T=100-160° C., 0.5% HMF LHSV=7.5-15 h$^{-1}$, GHSV=300 h$^{-1}$.

Figure 32:
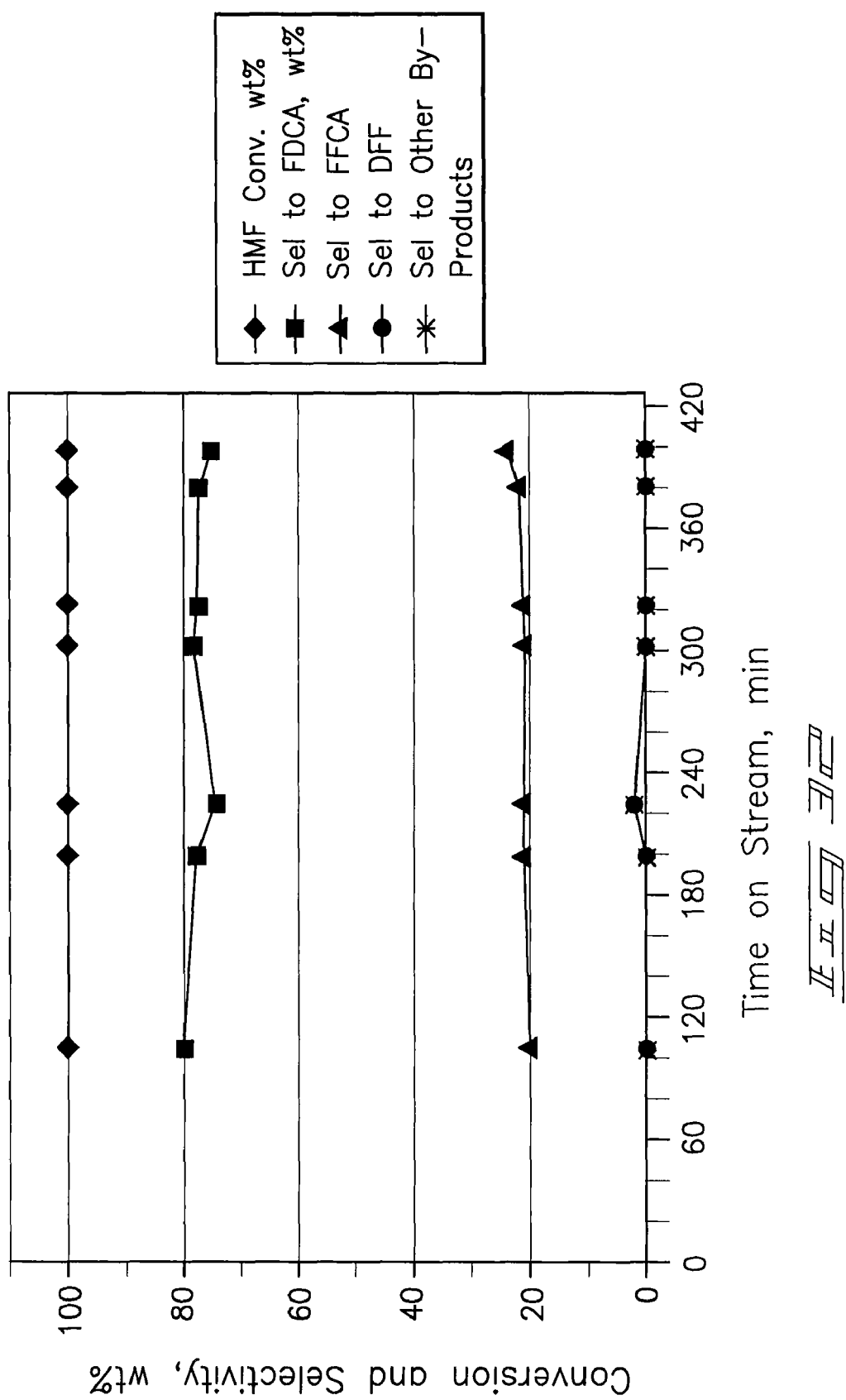

FIG. 32 shows HMF conversion and product selectivity as a function of time on stream utilizing the catalyst of FIG. 28. P=150 psig air, T=140° C., 0.5% HMF LHSV=7.5 h$^{-1}$, GHSV=300 h$^{-1}$.

Figure 33:
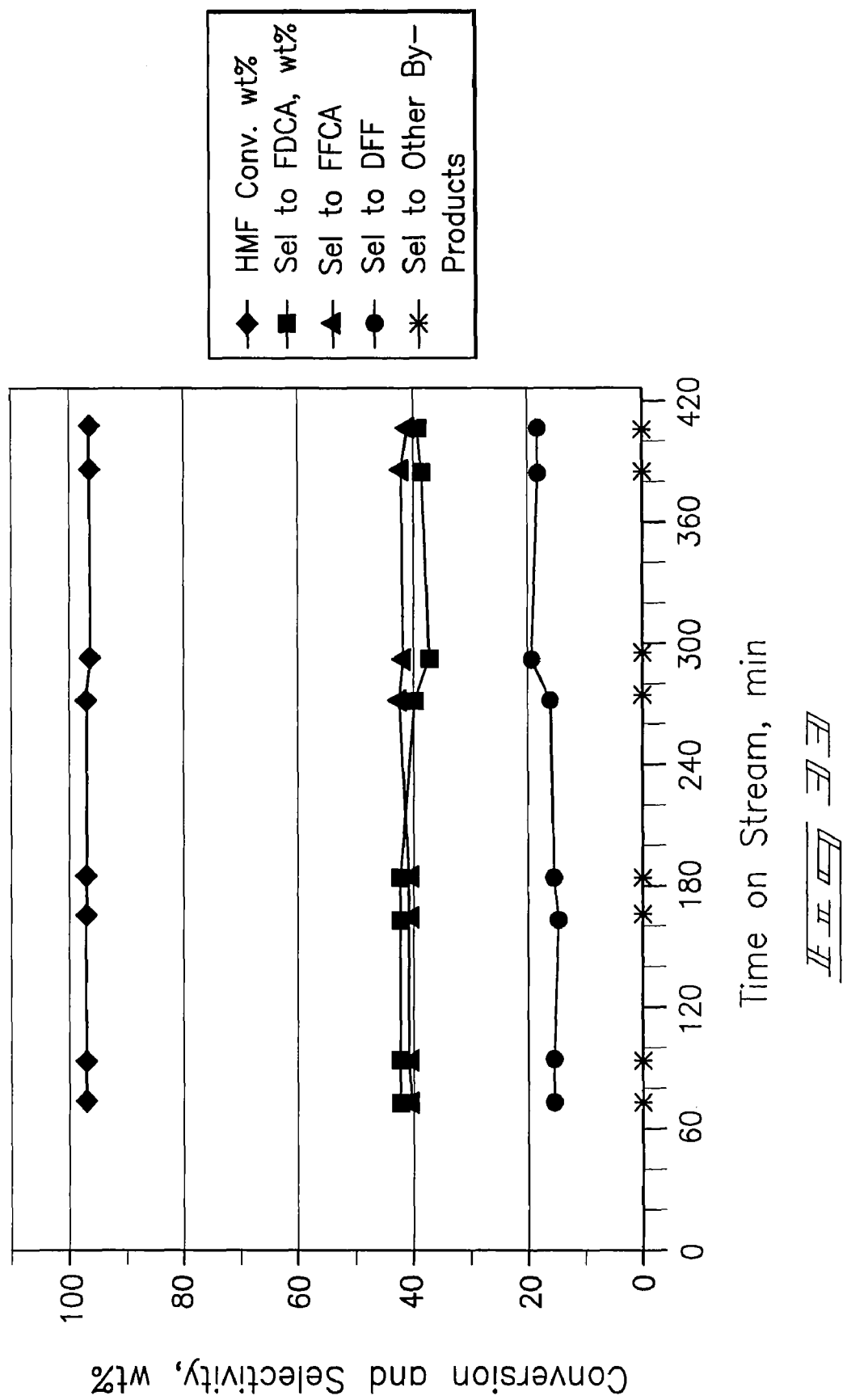

FIG. 33 shows HMF conversion and product selectivity as a function of time on stream utilizing the catalyst of FIG. 28 and the condition of FIG. 32 with the exception of decreased GHSV (GHSV=150 h$^{-1}$).

Figure 34:
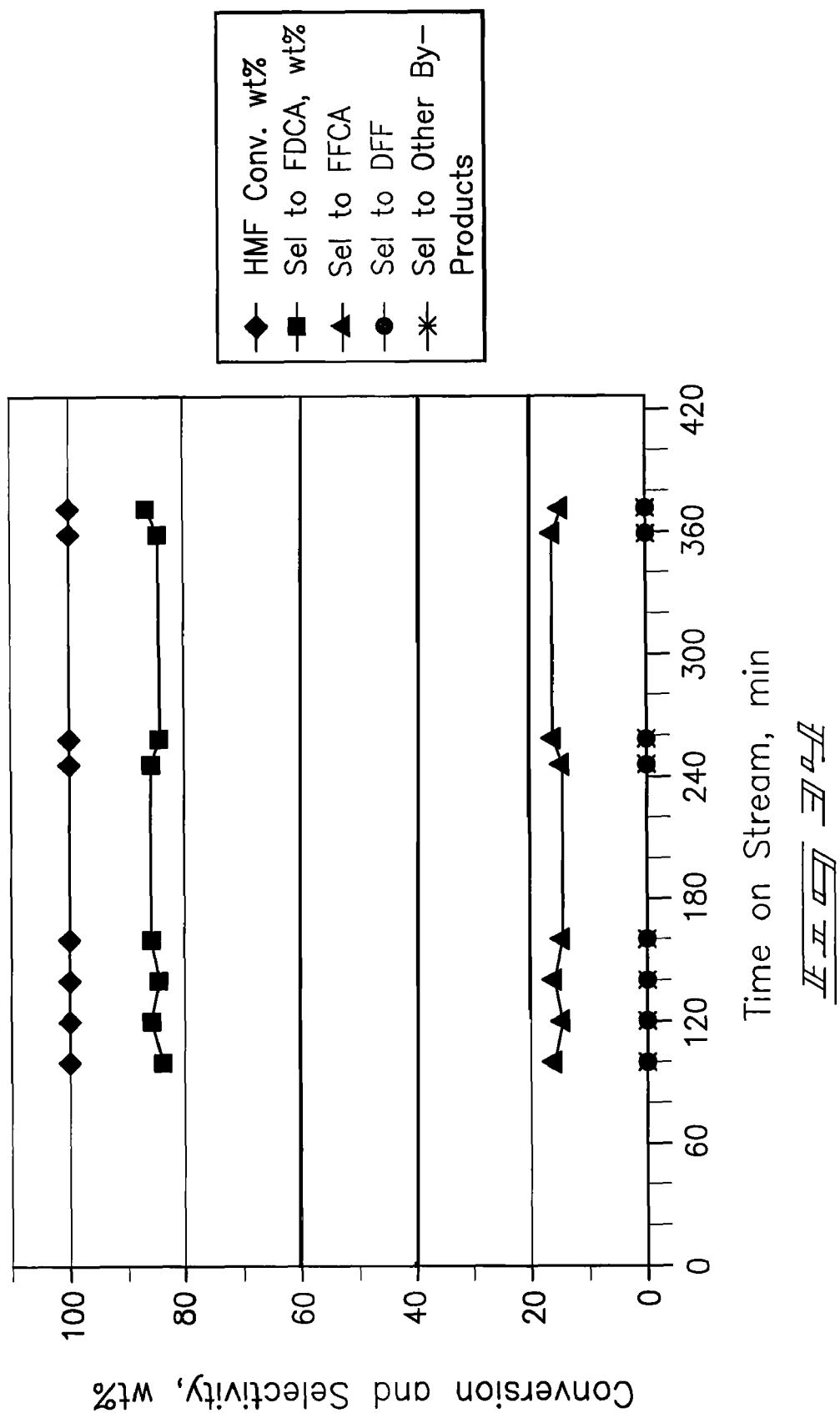

FIG. 34 shows HMF conversion and product selectivity as a function of time on stream utilizing the catalyst of FIG. 28 and the condition of FIG. 32 with the exception that P=500 psig air.

Figure 35:
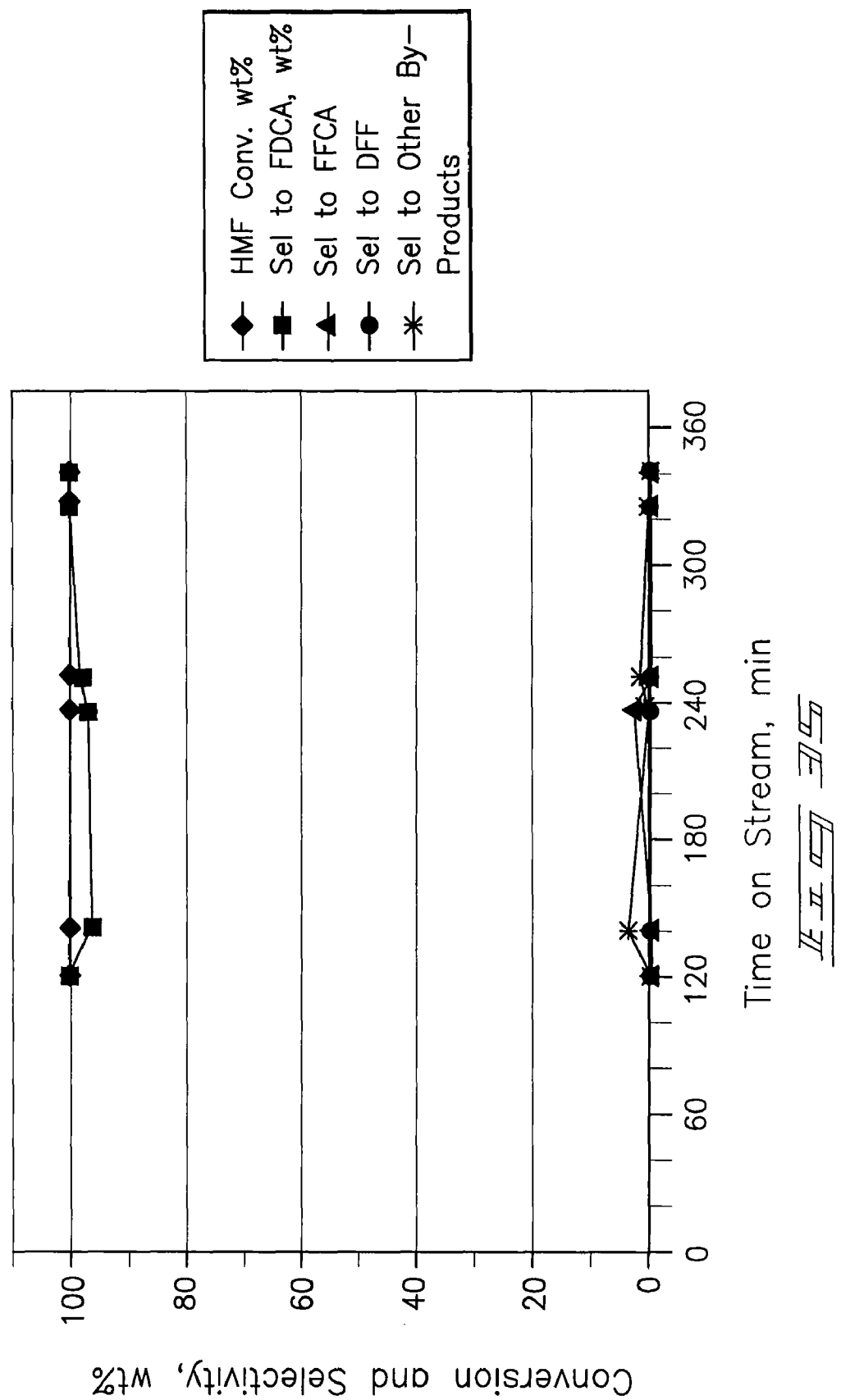

FIG. 35 shows HMF conversion and product selectivity as a function of time on stream utilizing the catalyst of FIG. 28 and the condition of FIG. 32 with the exception that GHSV=150 h$^{-1}$ and P=150 psig O$_2$.

Figure 36:
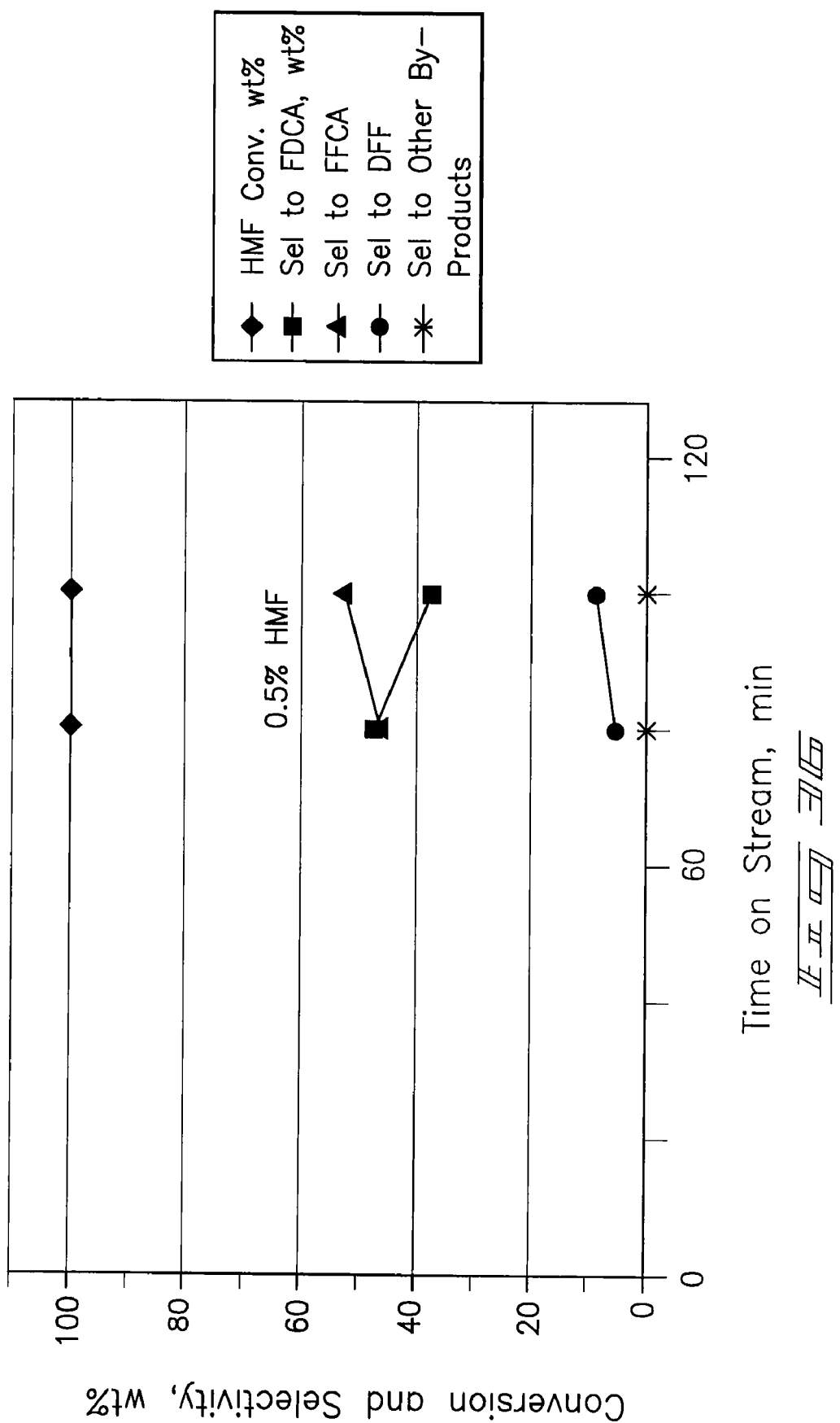

FIG. 36 shows HMF conversion and product selectivity as a function of time on stream utilizing the catalyst of FIG. 28 after Na$_2$CO$_3$ wash; 0.5% HMF, P=150 psig air, T=100° C., LHSV=7.5 h$^{-1}$, GHSV=300 h$^{-1}$.

Figure 37:
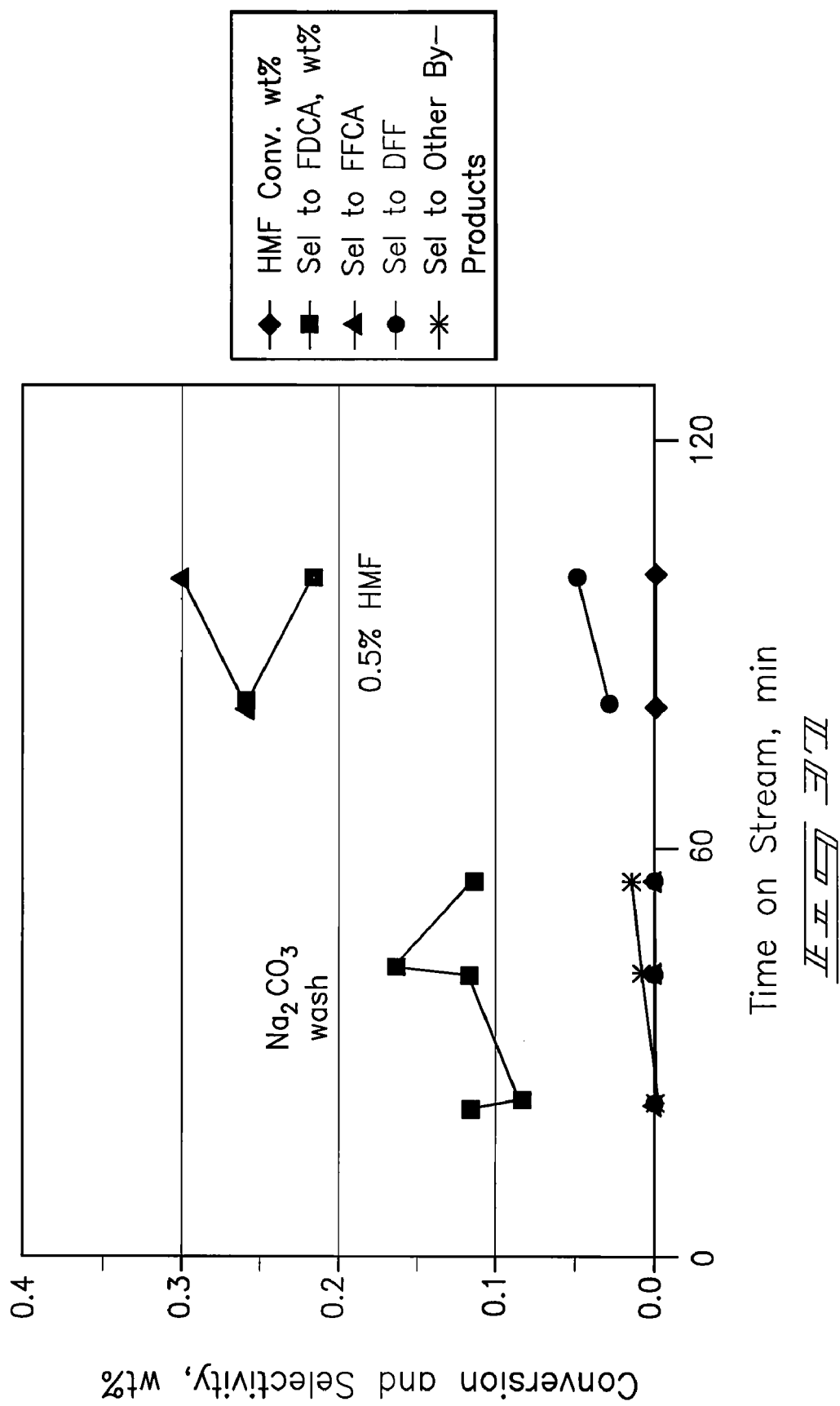

FIG. 37 shows the concentration in weight % versus time on stream of the indicated starting material, products and by-products utilizing the catalyst of FIG. 28 after a carbonate wash. 0.5% HMF, P=150 psig air, T=100° C., LHSV=7.5 h$^{-1}$, GHSV=300 h$^{-1}$.

Figure 38B:
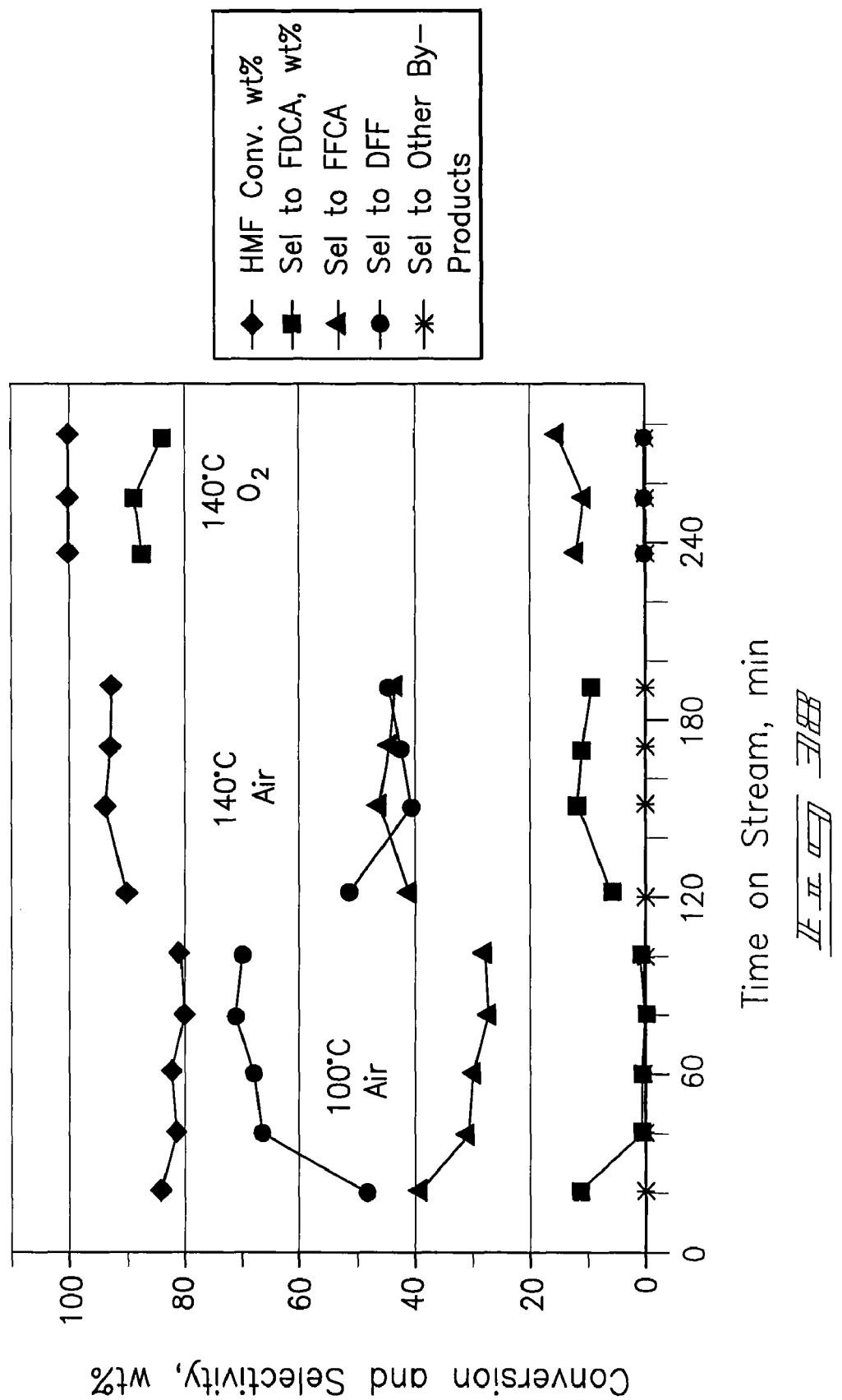

FIG. 38 shows HMF conversion and product selectivity as a function of time on stream utilizing the catalyst of FIG. 28 at varied temperature in the presence of either air or O$_2$. 1% HMF in 40% HOAc, 150 psig air/O$_2$, T=100-140° C., LHSV=7.5 h$^{-1}$, GHSV=300 h$^{-1}$.

Figure 39:
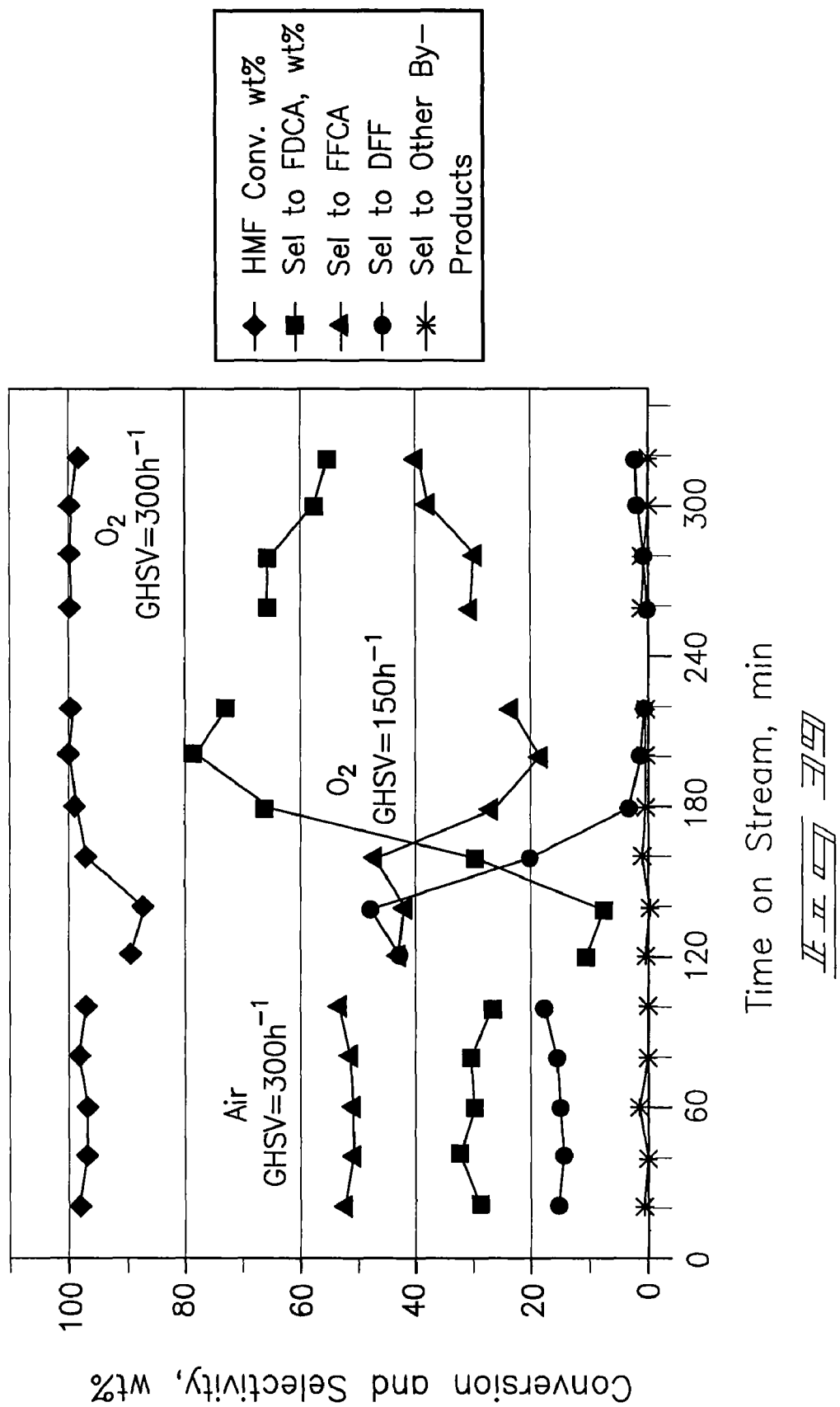

FIG. 39 shows HMF conversion and product selectivity as a function of time on stream utilizing the catalyst of FIG. 28 in the presence of either air or O$_2$ at varied GHSV. 0.5% HMF in 40% HOAc, P=150 psig air/O$_2$, T=140° C., LHSV=7.5 h$^{-1}$, GHSV=150-300 h$^{-1}$.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general, the invention pertains to methods of oxidizing hydroxymethyl furfural (HMF) in an aqueous solution. The oxidation process can be performed as a batch reaction or as a continuous flow process. A starting material is provided comprising HMF in water. Depending on the desired product, the mixture can be basic, neutral or acidic. Where an acidic aqueous solution solvent system is utilized, an appropriate acid can be added such as, for example, acetic acid. Due to the relatively low solubility of HMF oxidation products in neutral and acidic water, appropriate reactor designs can be utilized to accommodate solids formation. Feeds having up to 10% HMF have been successfully used in a batch reactor, and higher HMF concentrations are feasible. In a packed bed up-flow reactor the HMF concentration can preferably be less than or equal to about 3% by weight. Under mildly basic conditions, such as those created by providing $Na_2CO_3$ into the reaction mixture, products having carboxylic acid groups are present as the sodium salt and have increased solubilities. Solids formation and feed concentration are typically not problematic under these conditions. The addition of a strong base, such as NaOH, can lead to undesirable side reactions such as the Cannizzaro reaction.

weak bases can be present in the feed and do not need to be added slowly over the course of the reaction to prevent side reactions that tend to occur with strong bases such as NaOH.

Where continuous reaction is utilized in an up-flow packed bed reactor with a feed of about 1-3 wt % HMF, the liquid hourly space velocity (LHSV) can be, for example, from about 3 $h^{-1}$ to about 15 $h^{-1}$, and gas hourly space velocity (GHSV) can be for example from about 75 $h^{-1}$ to about 600 $h^{-1}$. These parameters can vary depending on the feed concentration and the reactor design and are presented for reference only.

The oxidation of HMF to fully oxidized product FDCA can occur with involvement of partially oxidized species DFF, HMFCA, and FFCA via the routes shown in the following diagram.

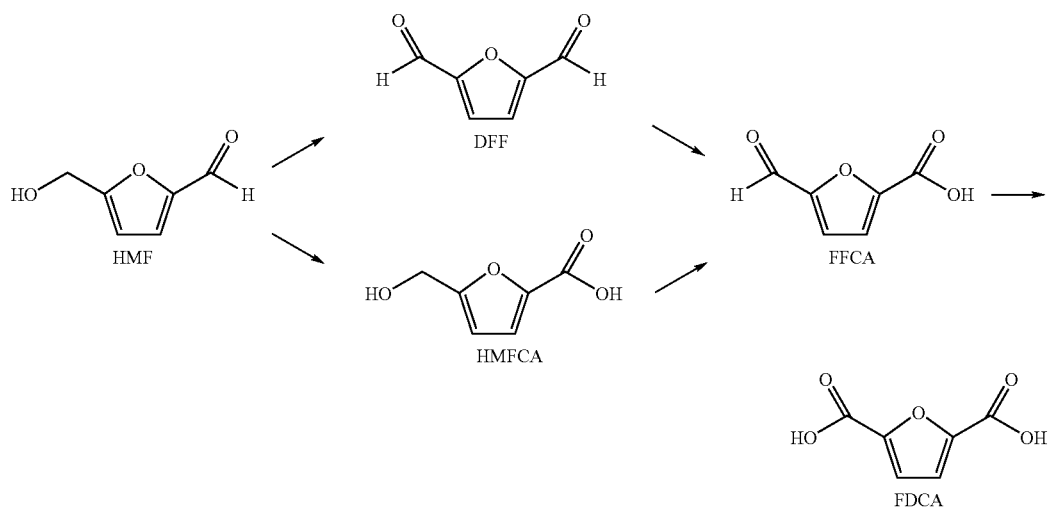

The starting material comprising HMF is provided into a reactor and at least one of air or $O_2$ is provided as oxidant. A pressure of from atmospheric to the pressure rating of the equipment can be utilized depending upon the desired reaction rate. A preferred pressure can typically be in the range of 150-500 psi. Similarly an appropriate reaction temperature can be from about 50° C. to about 200° C., with a preferred range of from 100° C. through about 160° C.

The starting material is contacted with a catalyst within the reactor. The catalyst typically comprises a metal on a support material. Preferably the metal comprises Pt. The support material can comprise, for example, C, $ZrO_2$, $Al_2O_3$, $SiO_2$, or $TiO_2$. The particular support material utilized can depend upon, for example, the desired oxidation product(s) (discussed below).

In particular instances, the reaction mixture can contain $Na_2CO_3$, or comparable weak base. Where $Na_2CO_3$ is utilized, such can be present in the mixture at a molar ratio of from 0.25 to 2.0 moles $Na_2CO_3$ to HMF, preferably at a molar ratio of from 0.5 to about 1.0 relative to HMF. The use of $Na_2CO_3$ or alternative carbonate bases is advantageous relative to conventional methodology. Other relatively weak bases (relative to NaOH) are contemplated such as those weaker than NaOH and stronger than the furan carboxylate product such that the furan carboxylate (FDCA, FFCA) remains in the soluble salt form. Possible alternative bases include metal carbonates, metal bicarbonates, metal phosphates, and metal hydrogen phosphates. These relatively As shown in the accompanying figures and as discussed further below, particular catalysts and sets of reaction conditions and parameters can favor selective production of one or more reaction products or intermediates. For example, under particular reaction conditions, HMF conversions of 100% were achieved with selectivity to FDCA as high as 98% relative to all other reaction products, intermediates and byproducts.

Studies utilizing various catalysts including those described herein for neutral and acidic feed solutions indicate that catalysts such as those described having high metal loading on low surface area (conditions that typically gives low dispersion of metal) produce the highest HMF conversion and FDCA selectivity. These results run counter to conventional wisdom that generally indicates best catalytic performance utilizing catalysts having high dispersion and high surface area.

Inorganic support materials can also be preferred for the present catalysts. Catalysts supported on carbon can result in product holdup and inhibition. Holdup can also increase generally with surface area even for those inorganic support materials, which tend to sorb less than carbon supports.

As indicated above, the fully oxidized product FDCA is relatively insoluble in water. Higher solubility can be attained in carboxylic acid solvent such as, for example, acetic acid/water mixtures. Table 1 shows the solubility of FDCA in various acetic acid/water mixtures. As indicated, the solubility in a 40/60 ratio $HOAc/H_2O$ is about twice the solubility in pure water. The oxidation of 0.5 weight % HMF in 40/60 HOAc/H$_2$O with 150 psi O$_2$ over a 5% Pt/ZrO$_2$ catalyst at 140° C. achieves 100% HMF conversion with up to about 80% selectivity to FDCA.

TABLE 1

Solubility of FDCA in acetic acid/water mixtures

| Vol % HOAc | Vol % H$_2$O | wt % 70° C. | wt % 25° C. |
|---|---|---|---|
| 0 | 100 | 0.327 | 0.086 |
| 40 | 60 | 0.779 | 0.153 |
| 50 | 50 | 0.746 | 0.173 |
| 60 | 40 | 0.596 | 0.171 |
| 70 | 30 | 0.592 | 0.143 |
| 90 | 10 | 0.458 | 0.138 |
| 100 | 0 | 0.193 | 0.080 |

As illustrated in FIGS. 1-11, HMF oxidation reactions performed utilizing 5% Pt supported on granular carbon can be utilized to selectively produce FFCA relative to individual alternative intermediates and oxidation products. In particular instances, such reactions under appropriate conditions can selectively produce FFCA relative to all other oxidation products, intermediates and byproducts.

Referring to FIGS. 12-13 studies were performed utilizing a 5% Pt/SiO$_2$ catalyst. Under appropriate reaction conditions the 5% Pt/SiO$_2$ catalyst can be utilized to selectively produce DFF relative to individual alternative oxidation products, intermediates and byproducts. In particular instances, DFF can be produced selectively relative to all other oxidation products, intermediates and by products (see FIG. 12). In the presence of Na$_2$CO$_3$, the 5% Pt/SiO$_2$ catalyst can be utilized to selectively produce FFCA as its Na salt (see FIG. 13).

The results of studies utilizing an alternative Pt/C catalyst are presented in FIGS. 14-17. As shown, an appropriate Pt/C catalyst can be utilized under the indicated reaction parameters to selectively produce FDCA relative to all other oxidation products, intermediates and byproducts.

Studies were performed utilizing a 5% Pt supported on Al$_2$O$_3$ catalyst, the results of which are presented in FIGS. 18-27. The 5% Pt supported on Al$_2$O$_3$ can be utilized to selectively produce FDCA and FFCA relative to alternative oxidation products and byproducts. Under alternative conditions the Pt/Al$_2$O$_3$ catalyst can also be utilized to selectively produce FDCA relative to all other oxidation products, intermediates and byproducts.

A 5% Pt supported on ZrO$_2$ catalyst was also utilized to perform HMF oxidation studies. The results of these studies are presented in FIGS. 28-39. The data indicates that the 5% Pt supported on ZrO$_2$ can produce 100% HMF conversion with selective production of FDCA relative to all other oxidation products intermediates and byproducts. Utilizing the same catalyst, an adjustment of reaction conditions can be utilized to produce, selectively, a product mixture of FDCA and FFCA.

Product isolation, separation and purification can be achieved based upon solubility differences between the compounds (HMF, individual intermediates, byproducts and FDCA) in aqueous and organic solvents.

In another aspect, the invention pertains to preparation of DFF from HMF. A mixture is provided containing HMF in an organic solvent. The mixture is contacted with the catalyst containing active γ-MnO$_2$ and is subjected to reflux temperature for a time of from about 6 hours to about 12 hours. The organic solvent can preferably be a chlorinated solvent such as methylene chloride. MnO$_2$ is removed by filtration followed by solvent removal. The resulting solids are dissolved in hot water and DFF is precipitated. HMF conversion is approximately 80% with DFF product selectivity nearly 100%. This methodology is advantageous relative to conventional methodology which utilizes MnO$_2$ to oxidize furandimethanol (FDM) as the starting material, where the yield of product DFF is reported as only 40%.

In yet another aspect of the invention pertains to a method of producing an oxidation catalyst. Extrudated ZrO$_2$ is provided and the extrudated ZrO$_2$ is calcined. The calcined ZrO$_2$ is crushed and sieved and is subsequently mixed with platinum (II) acetylacetonate to form a mixture. The mixture is subjected to rotary evaporation to form a product which is subsequently calcined. The product is activated by reducing under hydrogen and passivated under a flow of 2% O$_2$.

Example 1

Oxidation of HMF to FDCA in a Fixed-Bed Continuous Flow Reactor

A ⅜-inch stainless-steel thick-walled tube (0.065 inch wall thickness) was utilized as a tubular reactor. 4 mL (4.7254 g) of dry 5% Pt/ZrO$_2$ catalyst was placed in the reaction tube with 60-80 mesh glass beads at the inlet and outlet of the catalyst bed. The reactor tube was attached to a liquid-gas feed system and placed within a tube furnace. The catalyst was wetted with deionized water and reduced prior to testing at 150 psi pressure and ambient temperature with a hydrogen flow. After 30 minutes the hydrogen was shut off and the system was vented and purged with nitrogen.

Airflow of approximately 100 mL/min was established until the system pressure increased to 150 psig. Water was introduced at a flow rate of 0.5 mL/min with a high-pressure liquid pump and the airflow was then decreased to a flow rate of 20 mL/min (GHSV=300 h$^{-1}$). The temperature operating set point of the system was increased to 100° C. Upon achieving 100° C. a 0.5 weight % feed solution of HMF was fed into the catalyst bed at a rate of 0.2 mL/min (LHSV=3 h$^{-1}$). At 40-60 minute reaction time intervals (measured from the time feed was initiated) liquid samples of the product exiting the reactor were collected for liquid chromatography analysis. Liquid chromatography results for each sample taken showed 100% conversion of HMF with selectivity to FDCA attaining 98% within 40 minutes under these conditions. Conversion and selectivity remained constant for another 220 minutes of testing.

Example 2

Oxidation of HMF in a Batch Reactor

Batch oxidation of HMF was conducted in a 40 mL autoclave with a glass liner. 0.50 grams of 5% Pt on ZrO$_2$, 10 mL of deionized water and a magnetic stir bar were added into the glass liner. The vial and contents were sealed in the autoclave and were purged with nitrogen. The contents were then activated by reducing with hydrogen at room temperature. After 10 minutes the hydrogen was purged from the reactor with nitrogen. The nitrogen line was subsequently removed and no attempt was made to exclude air.

An oxygen line was attached to the reactor and the reactor was filled with oxygen. 0.51 grams of HMF in 5 mL of water was added to the autoclave with a syringe through a valve placed at the top of the autoclave cap. A magnetic stir plate was turned on and the reactor was pressurized to 150 psi with oxygen. The autoclave was heated to 100° C. After 6 hours reaction time a sample was removed from the reactor by cooling to 40° C., venting the oxygen to atmospheric pressure and withdrawing the sample through the top valve using a syringe and an 18 gauge needle. The sample was analyzed utilizing liquid chromatography and indicated that 80% of original HMF had reacted with approximately 68% conversion to DFF and 32% conversion to FFCA. The autoclave was charged to 150 psi with oxygen and was again heated to 100° C. for an additional 17 hours. The reactor was then cooled and vented and another sample removed. After a total of 23 hours reaction the HMF was completely depleted. Liquid chromatography revealed an absence of detectable DFF and FFCA. The primary product revealed utilizing liquid chromatography analysis was FDCA indicating complete oxidation of HMF. The only other product detected was levulinic acid, which resulted from the hydrolysis of HMF.

Example 3

Preparation of DFF from HMF 1.155 grams of HMF was dissolved in 50 mL of methylene chloride. 7.0606 grams of activated $MnO_2$ was added to the solution and the mixture was heated to reflux for 8 hours. The $MnO_2$ was removed from the reaction mixture by filtration and the solids were washed with additional solvent. The solvent was removed to produce and off-white solid. Liquid chromatography analysis of the solid indicated 80% DFF and 20% un-reacted HMF. A trace amount of FDCA was observed utilizing UV detection. The solid was dissolved in hot water and was subsequently cooled to precipitate DFF having a 98.5% purity. Selectivity of the oxidation reaction to DFF was substantially 100%.

Example 4

Preparation of 5% Pt on a $ZrO_2$ Support

Extrudated $ZrO_2$ received from Engelhard was calcined at 700° C. for 2 hours. The calcined $ZrO_2$ was crushed and sieved to 40-80 mesh size. 10.6318 grams of the crushed $ZrO_2$ was mixed at room temperature with 0.7593 grams of platinum(II) acetylacetonate in 50 mL flask. The flask was then mounted on a rotary evaporator and evacuated by a vacuum pump to reach 10 mmHg. The flask was rotated at 60 rpm for 10 minutes. After a thorough mixing the flask was heated to about 180° C. utilizing a heat gun. During the process the color of the catalyst changed from a light brown color to black. The temperature was then increased to about 240° C. Heating was stopped after approximately 20 minutes. The catalyst was then calcined in air for about 3 hours at 350° C. with a temperature ramp rate of 5° C. per minute.

Activation was carried out by reducing the catalyst in a fixed-bed reactor at 330° C. for 3 hours. The hydrogen flow rate was 40 mL/min. After reduction the reactor was cooled to room temperature under hydrogen and was then purged with helium for 30 minutes. Passivation was conducted by flowing 2% $O_2$ into the reactor at 40 mL/min overnight. The catalyst was unloaded from the reactor and was transferred to a storage container until use.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of oxidizing hydroxymethyl furfural (HMF), comprising:
    providing a starting material solution into a reactor, the solution having a pH less than or equal to 7, the solution comprising HMF and water;
    providing at least one of air and $O_2$ into the reactor; and
    contacting the starting material with a catalyst comprising Pt, on a support material comprising at least one of Zr, Al, Si, and Ti, the contacting being conducted at a reactor temperature of from about 50° C. to about 200° C., wherein the method selectively produces diformyl furan relative to all other products, intermediates and byproducts.

2. The method of claim 1 wherein the solution comprises acetic acid.

3. The method of claim 1 wherein the catalyst comprises 5% Pt on a $SiO_2$ support material.

4. The method of claim 1 wherein the support material comprises at least one of $ZrO_2$, $Al_2O_3$, $SiO_2$, and $TiO_2$.

5. The method of claim 3 wherein the acetic acid is present at a ratio of 40:60 relative to the water.

6. The method of claim 1 wherein air is provided to the reactor.

7. A method of oxidizing hydroxymethyl furfural (HMF), comprising:
    providing a solution into a reactor, the solution comprising HMF and water;
    providing at least one of air and $O_2$ into the reactor; and
    contacting the starting material with a catalyst comprising Pt and a support material, the support material comprising one or more of $ZrO_2$, $Al_2O_3$, $SiO_2$, and/or $TiO_2$, the contacting being conducted at a reactor temperature of from about 50° C. to about 200° C., wherein the method selectively produces diformyl furan relative to all other products, intermediates and byproducts.

8. The method of claim 7 wherein the solution has a pH less than or equal to 7.

9. The method of claim 7 wherein air is provided to the reactor.

10. The method of claim 7 wherein the solution consists essentially of HMF, water, and weak acid.

* * * * *

UNITED STATES PATENT AND TRADEMARK OFFICE
CERTIFICATE OF CORRECTION

| | |
|---|---|
| PATENT NO. | : 8,193,382 B2 |
| APPLICATION NO. | : 12/712100 |
| DATED | : June 5, 2012 |
| INVENTOR(S) | : Michael A. Lilga et al. |

It is certified that error appears in the above-identified patent and that said Letters Patent is hereby corrected as shown below:

Column 3, line 10 – Replace "7.5-15 $h^1$," with --7.5-15 $h^{-1}$,--

Column 3, line 15 – Replace "3-7.5 $h^1$," with --3-7.5 $h^{-1}$,--

Column 3, line 15 – Replace "=300 $h^1$," with --=300 $h^{-1}$,--

Column 7, line 32 – Replace "and by products" with --and byproducts--

Column 9, line 27 – Replace "produce and off-white" with --produce an off-white--

Signed and Sealed this
Twenty-eighth Day of August, 2012

David J. Kappos
*Director of the United States Patent and Trademark Office*